(12) United States Patent
Yamago

(10) Patent No.: US 8,664,372 B2
(45) Date of Patent: Mar. 4, 2014

(54) PROCESS FOR PRODUCING 1,2-TRANS-GLYCOSIDE COMPOUND

(75) Inventor: Shigeru Yamago, Osaka (JP)

(73) Assignee: Glytech, Inc., Kyoto (JP)

( * ) Notice: Subject to any disclaimer, the term of this patent is extended or adjusted under 35 U.S.C. 154(b) by 0 days.

(21) Appl. No.: 13/477,950

(22) Filed: May 22, 2012

(65) Prior Publication Data

US 2012/0232256 A1 Sep. 13, 2012

Related U.S. Application Data

(62) Division of application No. 11/884,544, filed as application No. PCT/JP2006/303519 on Feb. 20, 2006, now Pat. No. 8,212,013.

(30) Foreign Application Priority Data

Feb. 18, 2005 (JP) ................................. 2005-043220

(51) Int. Cl.
| | |
|---|---|
| *C07H 11/04* | (2006.01) |
| *C07H 15/04* | (2006.01) |
| *C07H 15/10* | (2006.01) |
| *C07H 15/14* | (2006.01) |
| *A61K 31/7024* | (2006.01) |
| *A61K 31/7028* | (2006.01) |

(52) U.S. Cl.
USPC ....................... 536/17.1; 514/53; 536/123.13

(58) Field of Classification Search
None
See application file for complete search history.

(56) References Cited

PUBLICATIONS

Buijsman, R. et al "Synthesis of heparin-like antithrombotics . . . " Bioorg. Med. Chem. (1999) vol. 7, pp. 1881-1890.*
Rabuka, David et al., "Synthesis and NMR characterization of the six regioisomeric monophosphates of octyl β-D-galactopyranosyl-(1→4)-2-acetamido-2-deoxy-β-D-glucopyranoside", *Carbohydrate Research*, 337 (2002) pp. 2127-2151.
Crich, David et al., "Chemistry of β-(Phosphatoxy)alkyl and β-(Acyloxy)alkyl Radicals. Migration Reactions: Scope and Stereoselectivity of β-(Phosphatoxy)alkyl Rearrangement. Mechanism of β-(Phosphatoxy)alkyl and β-(Acyloxy)alkyl Migration", *J. Am. Chem. Soc.*, 1995, 117, pp. 11455-11470.
Koch, Andreas et al., "112. Radical Rearrangements of 2-*O*-(Diphenoxyphosphoryl)glycosyl Bromides", *Helvetica Chimica Acta*, vol. 76 (1993) pp. 1687-1701.
Koch, Andreas et al., "Radical Rearrangement of 2-*O*-(Diphenylphosphoryl)glycosyl Bromides, A New Synthesis for 2-Deoxy Disaccharides and 2-Deoxy Ribonucleosides", *J. Org. Chem.*, 1993, 58, pp. 1083-1089.
Yamago, Shigeru et al., "Iterative Glycosylation of 2-Deoxy-2-aminothioglycosides and Its Application to the Combinatorial Synthesis of Linear Oligoglucosamines", *Angew. Chem. Int. Ed.*, 2004, 43, pp. 2145-2148.
Boons, G. "Recent developments in chemical oligosaccharide synthesis" Contemporary Org. Synth. (1996) vol. 3, pp. 173-200.
Banoub, J. et al "Synthesis of oligosaccharides . . . " Chem. Rev. (1992) vol. 92, pp. 1167-1195.
Garegg, P. "Synthesis and reactions of glycosides" Adv. Carbohyd. Chem. Biochem. (2004) vol. 59, pp. 69-134.
Degani, C. et al "Solvolysis of phosphoric acid esters . . . " JACS (1966) vol. 88, No. 17, pp. 4075-4082.
Bernlind, C. et al., "Synthesis, NMR, and conformational studies of methyl α-D-mannopyranoside 2-,3-,4-, and 6-monophosphates", *Carbohydrate Rersearch*, vol. 263, 1994, pp. 173-180.
Crich, D. et al., "Disarming, non-participating 2-*O*-protecting groups in manno- and rhamnopyranosylation: scope and limitations of sulfonates, vinylogous esters, phosphates, cyanates, and nitrates", *Tetrahedron: Asymmetry*, vol. 16, 2005, pp, 105-119.
Crich, D. et al., "Highly diastereoselective radical cyclization of a glucose-derived enol ether radical cation/phosphate anion pair", *Tetrahedron: Asymmetry*, vol. 14, 2003, pp. 2861-2864.
European Search Report Corresponding to European Application No. 06 71 4658; Dated; Jul. 11, 2012; 6 Pages.
Yamago, S. et al., "A New, Iterative Strategy of Oligosaccharide Synthesis Based on Highly Reactive β-Bromoglycosides Derived from Selenoglycosides", *Organic Letters*, 2001, vol. 3, No, 24, pp. 3867-3870.

* cited by examiner

*Primary Examiner* — Leigh Maier
(74) *Attorney, Agent, or Firm* — Myers Bigel Sibley & Sajovec, PA

(57) ABSTRACT

In preparing a glycoside compound from (a) a furanose compound or pyranose compound, and (b) an alcohol compound, a process for preparing a glycoside compound in which glycosidic bond locates selectively trans form relative to C-2 hydroxyl group, the process comprising using a furanose compound wherein the hydroxyl at the 2-position may have a substituent protected with a group A, or a pyranose compound which may have a substituent

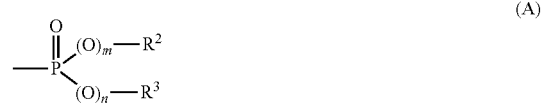

(A)

wherein $R^2$ and $R^3$ are the same or different and are each alkyl having 1 to 4 carbon atoms or aryl having or not having a substituent, or $R^2$ and $R^3$ are combined to form alkylene having 2 to 4 carbon atoms (the alkylene may be substituted with alkyl having 1 to 4 carbon atoms, or may have intervening phenylene), and m and n are each an integer of 0 or 1.

2 Claims, No Drawings

PROCESS FOR PRODUCING 1,2-TRANS-GLYCOSIDE COMPOUND

STATEMENT OF PRIORITY

This application is a divisional application of U.S. patent application Ser. No. 11/884,544, which is 35 U.S.C. §371 national phase application of International Application Serial No. PCT/JP2006/303519, filed Feb. 20, 2006, now U.S. Pat. No. 8,212,013, issued on Jul. 3, 2012, which claims the benefit, under 35 U.S.C. §119 (a), of Japanese Patent Application No. 2005-043220, filed Feb. 18, 2005, the disclosures each of which are incorporated herein by reference in their entireties.

TECHNICAL FIELD

The present invention relates to a process for selective preparation of 1,2-trans glycoside compounds.

BACKGROUND ART

Much attention has been directed in recent years to biological functions of oligosaccharides as the third biogenic polymers in the living body following nucleic acids and proteins. It has been found that the oligosaccharides present on the surfaces of cells have a wide variety of functions such as intercellular transmission of information and interaction between the oligosaccharide and an internal matrix such as virus. It is an urgent problem to clarify the structure-activity relationship for understanding many of biological processes involving oligosaccharides. However, naturally occurring oligosaccharide compounds possess microheterogeneity in structure in terms of branching, stereochemistry, and molecular weight, and chemically pure oligosaccharides are extremely difficult to separate from living body samples by purification procedures. In view of such problems, it is strongly desired to provide by chemical synthesis chemically pure oligosaccharide compounds having a clarified structure.

The 1,2-transglycoside linkage is a typical glycoside linkage which is generally found in oligosaccharides. The conventional method of preparing this glycoside bond stereoselectively uses 2-acyl protected glycosides as glycosyl donors, and the acyl group serves as stereodirecting group for the stereoselective formation of 1,2-trans glycosides by intramolecular participation. However, this process always has the problem of giving an ortho ester as a by-product.

The present inventor developed an iterative glycosylation reaction for preparing oligosaccharides by repeating the same reaction with use of thioglycoside only (Nonpatent Literature 1). This method was very effective for saccharide derivatives having an amino group at the 2-position, such as glucosamine, whereas it was not effective for other selective formation of ortho ester in the case where a saccharide derivative having a hydroxyl group at the 2-position, such as glucose, galactose or the like, was used.

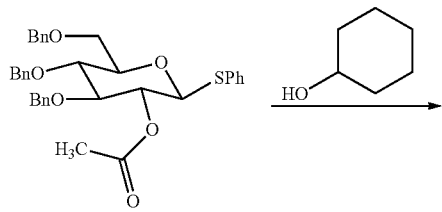

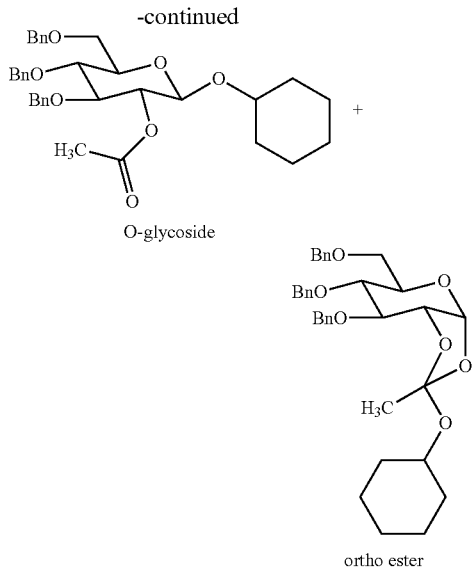

O-glycoside ortho ester wherein Ph is phenyl, and Bn is benzyl.

[Nonpatent Literature 1] Angew Chem. Int. Ed. 2004, 43, 2145.

An object of the present invention is to provide a process for selectively preparing a 1,2-transglycoside compound by inhibiting the formation of an o-ester by-product in saccharide derivatives having a hydroxyl group at the 2-position.

DISCLOSURE OF THE INVENTION

The present invention provides the process to be described below for preparing a 1,2-transglycoside compound, and 2-phosphonoyl-1,2-transglycoside compounds for use in the preparation process.

1. In preparing a glycoside compound from (a) a furanose compound or pyranose compound, and (b) an alcohol compound, a process for preparing a glycoside compound in which glycosidic bond locates selectively trans form relative to C-2 hydroxyl group, the process comprising using a furanose compound wherein the hydroxyl at the 2-position may have a substituent protected with a group A, or a pyranose compound which may have a substituent

(A)

wherein $R^2$ and $R^3$ are the same or different and are each alkyl having 1 to 4 carbon atoms or aryl having or not having a substituent, or $R^2$ and $R^3$ are combined to form alkylene having 2 to 4 carbon atoms (the alkylene may be substituted with alkyl having 1 to 4 carbon atoms, or may have intervening phenylene), and m and n are each an integer of 0 or 1.

2. A process for preparing a glycoside compound having a trans form according to claim 1 wherein the furanose compound is arabofuranose, erythrofuranose, glucofuranose, ribofuranose, threofuranose or xylofuranose, the pyranose compound is arabopyranose, altropyranose, glucopyranose, galactopyranose, glopyranose, mannopyranose, ribopyranose, xylopyranose or glucopyranuronic acid, and the alcohol compound is an aliphatic alcohol having 1 to 4 carbon atoms, alicyclic alcohol having 5 to 8 carbon atoms, aromatic alcohol, furanose, pyranose, aminopyranose, anhydrosugar, polysaccharide, N-acetylpyranose or glycerol.

3. A process for preparing a 2-phosphonoyl-1,2-transglycoside compound of the formula (3) comprising reacting an alcohol compound of the formula (2) with a 2-phosphonoylpyranose compound of the formula (1)

$$Q^1\!-\!Z \quad (1)$$

$Q^1 =$

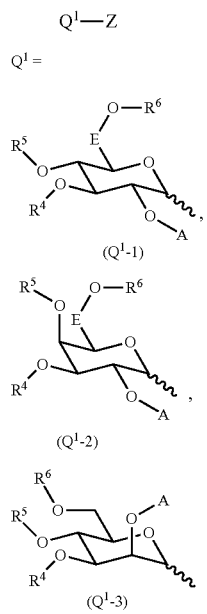

wherein Z is a group —S—$R^1$, group —SO—$R^1$, group —Se—$R^1$, group —O—C(=NH)$CX_3$, halogen atom, alkoxyl, alkenyloxy, group —P(O$R^1$)$_3$ or group —PO(O$R^1$)$_3$, $R^1$ being alkyl having 1 to 20 carbon atoms, aryl having or not having a substituent or heteroaromatic group, X being a halogen atom, $R^4$, $R^5$ and $R^6$ may be the same or different and are each a protective group for the saccharide hydroxyl group, E is methylene or carbonyl, and A is as defined above $$Q^2\text{-OH} \quad (2)$$

wherein $Q^2$ is alkyl having 1 to 4 carbon atoms, cycloalkyl having 5 to 8 carbon atoms and having or not having a substituent at an optional position or one of the following groups

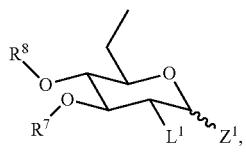
(Q²-1)

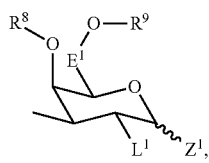
(Q²-2), (Q²-3)

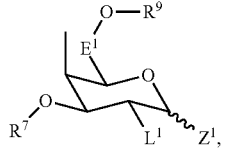
(Q²-4), (Q²-5)

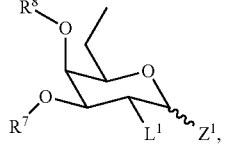
(Q²-6), (Q²-7)

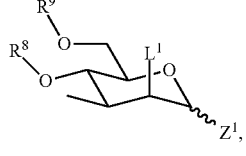
(Q²-8)

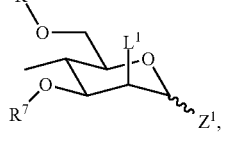
(Q²-9)

wherein $L^1$ is a group —O$A^1$, —OG or —N($J^1$)($J^2$), $A^1$ being a group shown below, G being a protective group for the saccharide hydroxyl, and $J^1$ and $J^2$ being each a hydrogen atom or a protective group for amino

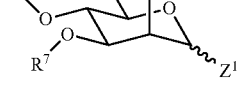
(A¹)

$R^{2'}$ and $R^{3'}$ are the same or different and are each alkyl having 1 to 4 carbon atoms or aryl having or not having a substituent, or $R^{2'}$ and $R^{3'}$ are combined with each other to form alkylene having 2 to 4 carbon atoms (the alkylene may be substituted with alkyl having 1 to 4 carbon atoms or may have an intervening phenylene), m' and n' are each an integer of 0 or 1. $Z^1$ is a group —S—$R^{1'}$, group —SO—$R^{1'}$, group —Se—$R^{1'}$, group —O—C(=NH)CX'$_3$, halogen atom, alkoxyl, alkenyloxy, group —P(OR$^{1'}$)$_3$, group —PO(OR$^{1'}$)$_3$ or —OG$^1$, R$^{1'}$ being alkyl having 1 to 20 carbon atoms, aryl having or not having a substituent or heteroaromatic group, X' being a halogen atom, G$^1$ being a protective group for the saccharide hydroxyl, R$^7$, R$^8$ and R$^9$ may be the same or different and are each a protective group for the saccharide hydroxyl group, E$^1$ is methylene or carbonyl

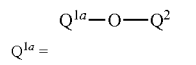

(3)

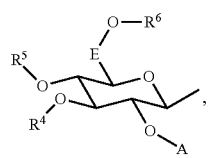

(Q$^{1a}$-1)

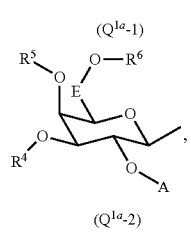

(Q$^{1a}$-2)

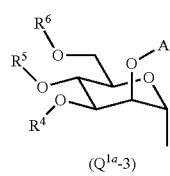

(Q$^{1a}$-3)

wherein Q$^2$, A, R$^4$, R$^5$ and R$^6$ are as defined above.

4. A process for preparing a 2-phosphonoyl-1,2-transglycoside compound of the formula (3a) comprising reacting an alcohol compound of the formula (2a) with a 2-phosphonoylpyranose compound of the formula (1)

Q$^{2a}$-OH (2a)

wherein Q$^{2a}$ is one of the groups given below, A$^1$, R$^7$, R$^8$, R$^9$ and E$^1$ are as defined above, Z$^2$ is a group —S—R$^{1'}$, group —SO—R$^{1'}$, group —Se—R$^{1'}$, group —O—C(=NH)CX'$_3$, halogen atom, alkoxyl, alkenyloxy, group —P(OR$^{1'}$)$_3$ or group —PO(OR$^{1'}$)$_3$, and R$^{1'}$ and X' are as defined above

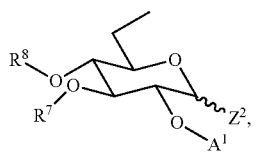
(Q$^{2a}$-1)

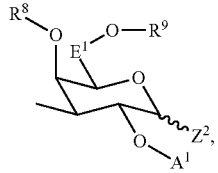
(Q$^{2a}$-2)

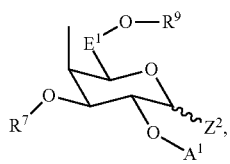
(Q$^{2a}$-3)

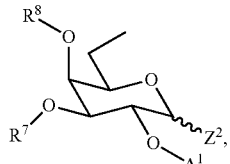
(Q$^{2a}$-4)

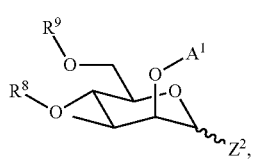
(Q$^{2a}$-5)

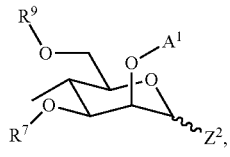
(Q$^{2a}$-6)

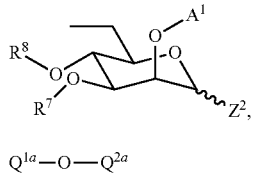
(Q$^{2a}$-7)

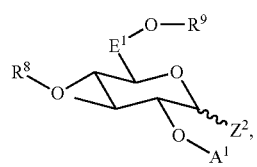
(Q$^{2a}$-8)

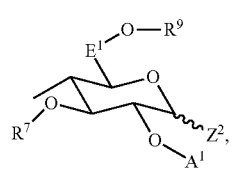
(Q$^{2a}$-9)

Q$^{1a}$—O—Q$^{2a}$ (3a)

wherein Q$^{1a}$ and Q$^{2a}$ are as defined above.

5. A process for preparing a 2-phosphonoyl-1,2-transglycoside compound comprising repeating the step of reacting an alcohol compound with a 2-phosphonoyl-1,2-transglycoside compound of the formula (3a) at least once.

6. A process for preparing a 1,2-transglycoside compound of the formula (4) comprising reacting a base with a 2-phosphonoyl-1,2-transglycoside compound of the formula (3)

Q$^3$—O—Q$^4$ (4)

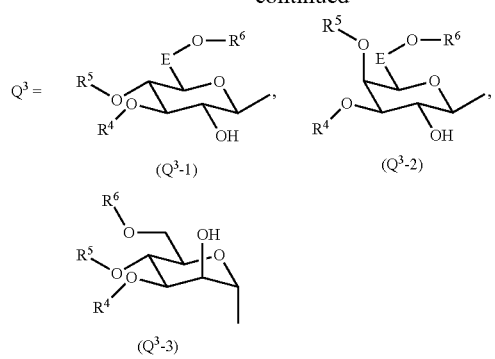

wherein $R^4$, $R^5$, $R^6$ and E are as defined above, and $Q^4$ is alkyl having 1 to 4 carbon atoms, cycloalkyl having 5 to 8 carbon atoms and having or not having a substituent at an optional position or one of the groups given below

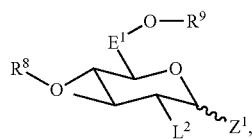

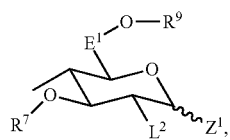

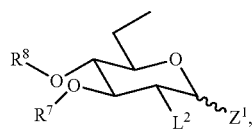

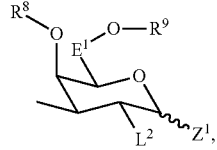

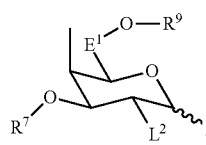

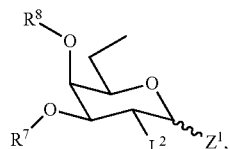

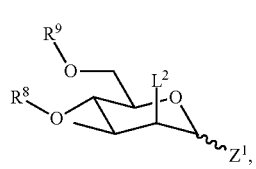

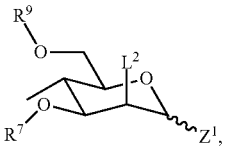

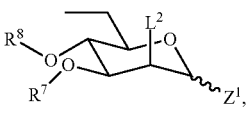

wherein $L^2$ is the group —OH, —OG or —N($J^1$)($J^2$), and $Z^1$, $R^7$, $R^8$, $R^9$, $E^1$, G, $J^1$ and $J^2$ are as defined above.

7. A phosphonoylpyranose compound of the formula (1).

8. A 2-phosphonoyl-1,2-transglycoside compound of the formula (3).

9. A 2-phosphonoyl-1,2-transglycoside compound of the formula (3a).

According to the present invention, a glycoside compound having a 1,2-trans stereochemistry can be prepared selectively by using a 2-phosophonoylfuranose compound or 2-phosophonoylpyranose compound comprising a furanose compound or pyranose compound wherein the hydroxyl group at the 2-position is protected with a specific phosphoric acid ester.

The substituents given below are herein described.

Examples of alkyl groups having 1 to 4 carbon atoms are methyl, ethyl, n-propyl, isopropyl, n-butyl, isobutyl, sec-butyl. tert-butyl, etc.

Examples of aryl groups can be phenyl, naphthyl, etc. These groups may have a substituent at an optional position. Examples of substituents are a hydrogen atom, alkyl having 1 to 4 carbon atoms, etc. Examples of halogen atoms are fluorine atom, chlorine atom, bromine atom and iodine atom. The same or different substituents may be present, and one to a number of substituents that can serve as such can be present.

Examples of alkylene groups having 2 to 4 carbon atoms are dimethylene, trimethylene and tetramethylene. These groups may be substituted with alkyl having 1 to 4 carbon atoms at an optional position, or may have intervening phenylene. More specific examples are the group —(CH$_2$)$_2$—, group —(CH$_2$)$_3$—, group —(CH$_2$)$_4$—, group —C(CH$_3$)$_2$C(CH$_3$)$_2$—, group —CH$_2$CH(CH$_3$)CH$_2$—, group —CH(CH$_3$)CH$_2$CH(CH$_3$)—, group —C(CH$_3$)$_2$CH$_2$CH$_2$—, group —CH$_2$C(CH$_3$)$_2$CH$_2$—, —CH$_2$CH$_2$—C$_6$H$_4$—CH$_2$—, etc.

Examples of alkoxyl groups are those having 1 to 4 carbon atoms, such as methoxy, ethoxy, n-propoxy, isopropoxy, n-butoxy, isobutoxy, sec-butoxy and tert-butoxy.

Examples of alkenyloxy groups are those having 2 to 4 carbon atoms such as vinyloxy, propenyloxy and butenyloxy.

Examples of groups for protecting the saccharide hydroxyl group are not limited particularly insofar as they are useful for protecting the hydroxyl group of saccharide compounds. Examples of such groups are benzyl, methoxymethyl, tert-butyldimethylsilyl, triisopropylsilyl, benzoyl, acetyl, pivaloyl, levulyl, etc. Two adjacent hydroxyl groups may provide a ring with methylene, ethylene, isopropylidene or benzylidene.

Examples of cycloalkyl groups having 5 to 8 carbon atoms are cyclopentyl, cyclohexyl, cycloheptyl and cyclooctyl. These groups may have a substituent at an optional position. Examples of substituents are alkyl groups having 1 to 4 carbon atoms. More specific examples are 4,5-dimethylpentyl, 4-methylhexyl, 3,5-dimethylhexyl, 4-tert-butylhexyl, 2,4,6-trimethylhexyl, etc.

According to the present invention, 1,2-transglucoside compounds are prepared using a furanose compound or pyranose compound wherein the hydroxyl group at the 2-position is protected with a group A and which may have a substituent, and an alcohol compound $$\begin{matrix} & \text{O} \\ & \| \\ -\text{P} & -(\text{O})_m-\text{R}^2 \\ & \diagdown \\ & (\text{O})_n-\text{R}^3 \end{matrix} \quad (A)$$

wherein $R^2$, $R^3$, m and n are as defined above.

The furanose compound to be used is not particularly limited insofar as it has a hydroxyl group at the 2-position. For example, the furanose compound is arabofuranose, erythrofuranose, glucofuranose, ribofuranose, threofuranose or xylofuranose. These furanose compounds may have a substituent. Examples of substituents are protective groups for saccharide hydroxyl groups, and groups which comprise a monosaccharide or polysaccharide and which may have a hydroxyl group as protected with a protective group.

The pyranose compound to be used is not limited specifically insofar as it has a hydroxyl group at the 2-position. For example, the pyranose compound is arabopyranose, altropyranose, glucopyranose, galactopyranose, glopyranose, mannopyranose, ribopyranose, xylopyranose or glucopyranuronic acid, These pyranose compounds may have a substituent. Examples of substituents are protective groups for saccharide hydroxyl groups, and groups which comprise a monosaccharide or polysaccharide and which may have a hydroxyl group as protected with a protective group.

Examples of groups A are given below.

(A-1) phosphate with two O—$C_6H_5$ groups (A-2) cyclic phosphate with tetramethyl ethylene diol (four $CH_3$ groups)

(A-3) six-membered cyclic phosphate (1,3-propanediol)

(A-4) six-membered cyclic phosphate with one $CH_3$ substituent (A-5) six-membered cyclic phosphate with two $CH_3$ groups on one carbon (A-6) six-membered cyclic phosphate with two $CH_3$ groups (A-7) six-membered cyclic phosphate with (S),(S) $CH_3$ groups (A-8) six-membered cyclic phosphate with (R),(R) $CH_3$ groups (A-9) six-membered cyclic phosphate with two gem-dimethyl groups (A-10) benzo-fused seven-membered cyclic phosphate (A-11) phosphine oxide with two $C_6H_5$ groups Among these, especially preferable to use are the groups (A-3) and (A-5).

For a simplified description, the present invention as practiced by using pyranose compounds only will be described below, whereas the invention can be practiced similarly with use of furanose compounds.

The pyranose compound wherein the hydroxyl group at the 2-position is protected with a group A can be prepared by reacting a phosphoric acid halide of the formula (5) with a pyranose compound $$A-X^3 \quad (5)$$

wherein A is as defined above, and $X^3$ is a halogen atom.

For example, the 2-phosphonoyl-1,2-transpyranose compound of the formula (1) can be prepared according to Reaction Formula-1 given below.

Reaction Formula-1 pyranose compound (6-1) with $R^5O$, $R^4O$, $R^6O$, OH, Z substituents reacted with $A-X^3$ (5)

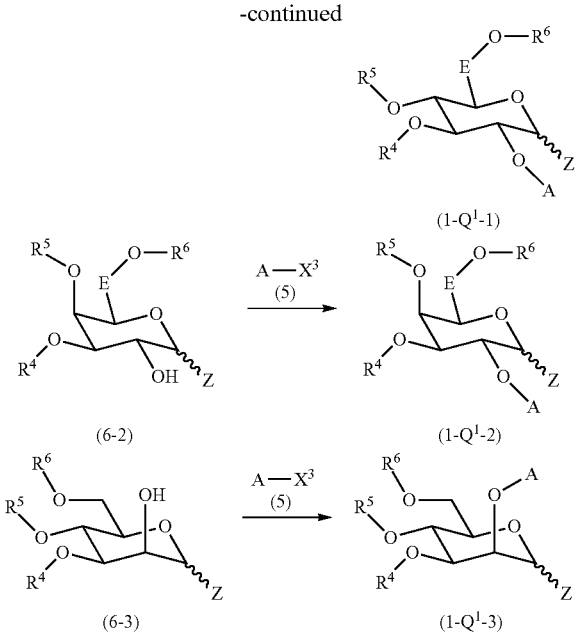

wherein A, R$^4$, R$^5$, R$^6$, Z and X$^3$ are as defined above.

According to Reaction Formula-1, the 2-phosphonoyl-1,2-transpyranose compound of the formula (1-Q$^1$-1), (1-Q$^2$-1) or (1-Q$^3$-1) corresponding to the compound of the formula (1) can be prepared by reacting the phosphoric acid halide of the formula (5) with a pyranose compound of the formula (6-1), (6-2) or (6-3).

This reaction is conducted usually in a solvent by causing a base to act on the pyranose compound of the formula (6-1), (6-2) or (6-3) and thereafter causing the phosphoric acid halide of the formula (5) to act on the resulting product. The solvent to be used is not limited specifically insofar as it is inert to the reaction. Examples of useful solvents are hexane, heptane, pentane and like aliphatic hydrocarbons, cyclohexane and like aliphatic hydrocarbons, benzene, toluene, xylene and like aromatic hydrocarbons, dichloromethane, chloroform, 1,2-dichloroethane, 1,1,1-trichloroethane, tetrachloroethylene, trichloroethylene, carbon tetrachloride, chlorobenzene, dichlorobenzene and like hydrocarbon halides, diethyl ether, isopropyl ether, tetrahydrofuran, dioxane, monoglyme and like ethers, N,N-dimethylformamide, N,N-dimethylacetamide, 1,3-dimethylimidazolidinone and like amides, dimethyl sulfoxide and like sulfoxides, or solvent mixtures of such solvents. Especially preferable among these are ethers, amides and sulfoxides.

These solvents are used in an amount of about 1 to about 100 liters, preferably about 5 to about 20 liters, per kg of the pyranose compound of the formula (6-1), (6-2) or (6-3).

Examples of useful bases are sodium carbonate, potassium carbonate and like alkali metal carbonates, sodium hydride and like alkali metal hydrides, triethylamine, pyridine, DBU and like organic bases, and butyl lithium, lithium diisopropylamide, lithium bistrimethylsilylamide and like lithium salts.

These bases can be used singly, or at least two of them are usable in combination. These bases are used in an amount of 1 to 10 equivalents, preferably 1 to 5 equivalents, based on the pyranose compound of the formula (6-1), (6-2) or (6-3).

Although the pyranose compound of the formula (6-1), (6-2) or (6-3) and the phosphoric acid halide of the formula (5) can be used in a desired ratio, it is desirable to use 1.0 to 2.0 moles of the latter per mole of the former.

The reaction temperature, which can be set to a desired value in the range of −20 to 100° C., is usually preferably 0 to 30° C. The reaction time is not limited particularly and is usually about 30 minutes to about 3 hours.

The 2-phosphonoylpyranose compound which is obtained by the above procedure and wherein the hydroxyl group at the 2-position is protected with a phosphoric acid ester is a novel compound which has not been disclosed in literature.

The pyranose compounds of the formulae (6-1), (6-2) and (6-3) can be prepared, for example, by the known conventional processes to be described below.

The compound of the formula (6-1) glucose

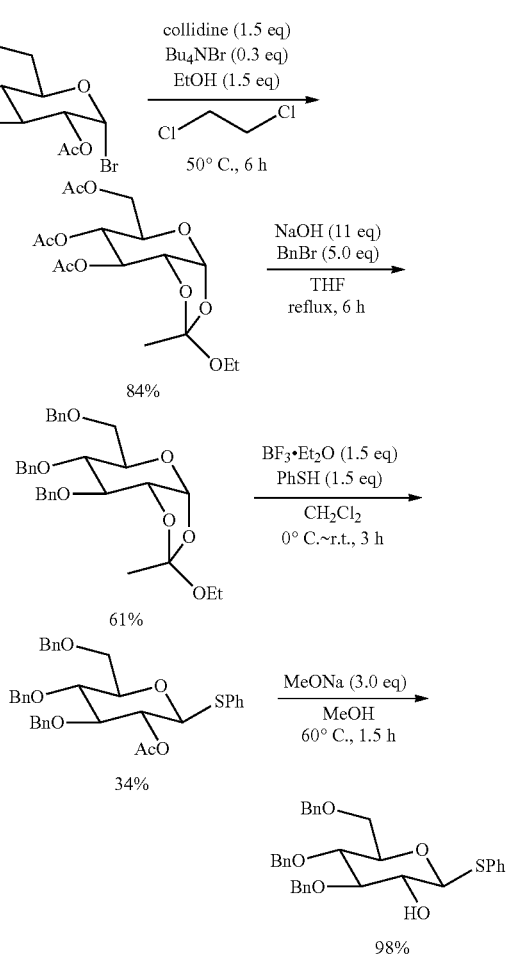

REFERENCE LITERATURE

Carbohydr. Res. 1992, 236, 73.
Can. J. Chem. 1965, 43, 2199.
Org. Lett. 2004, 3797.

The compound of the formula (6-2) galactose

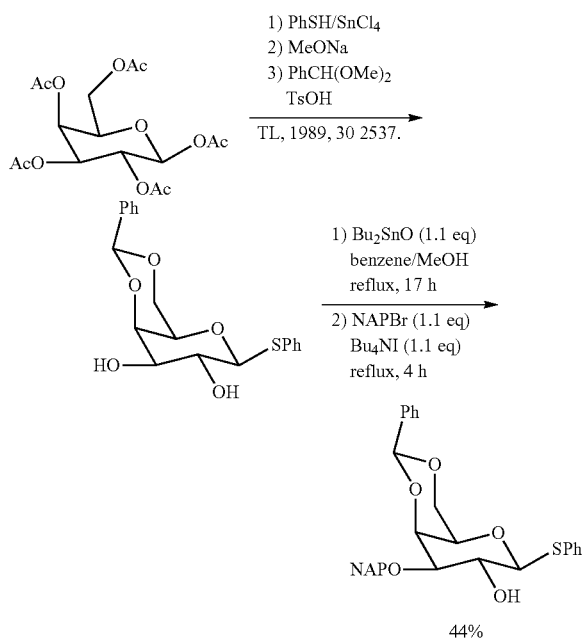

TL: Tetrahedron Lett. 1989, 30, 2537.
NAP: 2-naphthylmethyl
The compound of the formula (6-3) mannose

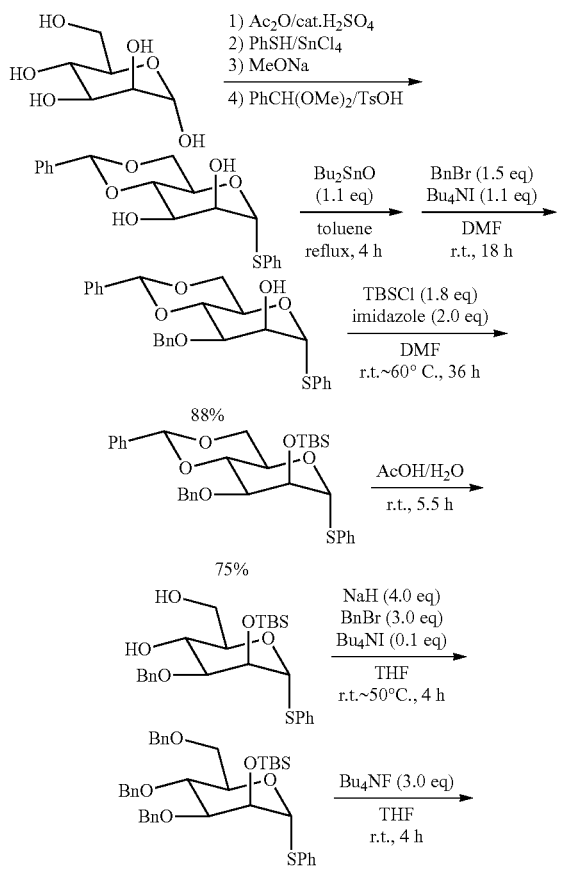

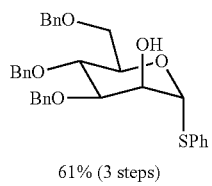

61% (3 steps)

The alcohol compound to be used is not limited particularly insofar as the compound forms a glycoside linkage with the 1-position of the pyranose. Examples of useful alcohol compounds are aliphatic alcohols having 1 to 4 straight-chain or branched-chain carbon atoms, such as methanol, ethanol, propanol, isopropanol and butanol, alicyclic alcohols having 5 to 8 carbon atoms, such as cyclohexanol, cyclopentanol and cyclooctanol, aromatic alcohols such as phenol, cresol and naphthol, furanoses such as arabofuranose, erythrofuranose, glucofuranose, galactofuranose, fructofuranose, ribofuranose, deoxyribofuranose, threofuranose and xylofuranose, pyranoses such as arabopyranose, altropyranose, glucopyranose, galactopyranose, glopyranose, mannopyranose, ribopyranose, xylopyranose and glucopyranuronic acid, aminopyranoses such as 2-amino-2-deoxygalactopyranose and 2-amino-2-deoxyglucopyranose, anhydrosugars such as glucosamine, polysaccharides such as gentiobiose, sucrose, cellobiose, lactose, allolactose, maltose, trehalose, N-acetylactosamine, kanamycin and kasugamycin, N-acetylpyranoses such as 2-acetamido-2-deoxygalactopyranoe, 2-acetamido-2-deoxyglucopyranose, 2-acetamido-2-deoxymannopyranose and aspartylglycosylamine, glycerols, etc. These compounds may have a substituent that will not adversely affect the reaction.

The glycoside compound of trans form can be obtained by causing an alcohol compound to act on the pyranose compound wherein the hydroxyl group at the 2-position is protected with the group A. This reaction can be conducted by a known conventional process comprising activating the carbon at the 1-position of the pyranose compound and causing the alcohol to act on the compound. The reaction can be represented, for example, by Reaction Formula-2 given below.

Reaction Formula-2

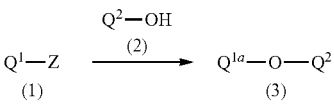

wherein $Q^1$, $Q^{1a}$ and $Q^2$ are as defined above, Z is a group —S—$R^1$, group —SO—$R^1$, group —Se—$R^1$, group —O—C(=NE)$CX_3$, halogen atom, alkoxyl, alkenyloxy, group —P(O$R^1$)$_3$ or group —PO(O$R^1$)$_3$, $R^1$ being alkyl having 1 to 20 carbon atoms, aryl having or not having a substituent or heteroaromatic group, X being a halogen atom.

Examples of alkyl groups having 1 to 20 carbon atoms are methyl, ethyl, n-propyl, isopropyl, n-butyl, isobutyl, sec-butyl, tert-butyl, hexyl, octyl, decyl, dodecyl, hexadecyl, octadecyl, eicosyl, etc. Aryl groups which may have a substituent are the same as those already mentioned. The heteroaromatic group is, for example, pyridyl.

The 2-phosphonoyl-1,2-transglycoside compound of the formula (3) can be prepared by activating a 2-phosphonoylpyranose compound of the formula (1) as the pyranose compound wherein the hydroxyl group at the 2-position is protected, and thereafter causing an alcohol compound of the formula (2) to act on the activated compound.

In the case where Z is a group —S—$R^1$ or group —SO—$R^1$ in the 2-phosphonoylpyranose compound of the formula (1), the alcohol compound of the formula (2) can be reacted with the compound (1), for example, according to J. Am. Chem. Soc., 2001, 123, 9015 or "Carbohydrates in Chemistry and Biology," Wiley-VCH, 2000, Vol. 1, Chap. 4 (pp. 93-134), after the compound (1) has been activated.

This reaction is conducted in a solvent. Examples of useful solvents are dichloromethane, dichloroethane, tetrachloroethane and like hydrocarbon halides, toluene and like aromatic hydrocarbons, etc., among which dichloromethane and tetrachloroethane are desirable. The solvent should be made anhydrous to such an extent as to avoid the influence on the reaction. The solvent is used in an amount of 1 to 100 liters, preferably about 5 to about 50 liters, per kg of the compound (1).

The compound (1) is activated by causing 2,6-tert-butyl-4-methylpyridine (DTBMP), benzenesulfinylpyridine (BSP), trifluoromethanesulfonic anhydride ($Tf_2O$) or the like to act thereon.

DTBMP is used in an mount of about 1 to about 5 mole equivalents, BSP in an amount of about 1 to 2 equivalents, or $Tf_2O$ in an amount of about 1 to about 2 equivalents, per mol of the compound (1).

The reaction is conducted preferably in an anhydrous system, preferably in the presence of a dehydrating agent such as a molecular sieve (molecular sieve 4A).

Since the activated compound obtained by the intermediate step is low in thermal stability, it is desired to conduct the reaction at a low temperature of up to −40° C.

The alcohol compound (2) is added to the compound (1) as activated in this way, whereby the 2-phosphonoyl-1,2-glycoside compound (3) can be prepared.

The alcohol compound (2) is used in an amount of 0.8 to 3 mole equivalents, preferably 1.0 to 2.0 mole equivalents, per mole of the compound (1).

The reaction temperature can be set to a desired value in the range of −80 to −40° C., and is usually preferably −70 to −45° C. Although not limited particularly, the reaction time is usually about 1 minute to about 1 hour.

The 2-phosphonoylpyranose compound of the formula (1) can be activated, for example, according to the method described in the following literature.
(a) In case where Z is a group —O—C(=NH)$CX^1{}_3$; "Preparative Carbohydrate Chemistry", Marcel Dekker, Inc., 1997, Chap 12 (pp 283-312) and "Carbohydrates in Chemistry and Biology", Wiley-VCH, 2000, Vol. 1, Chap 2 (pp 5-59)
(b) In case where Z is chlorine atom or bromine atom; Angew. Chem. Int. Ed. 1982, 21, 155-224
(c) In case where Z is fluoride atom; "Preparative Carbohydrate Chemistry", Marcel Dekker, Inc., 1997, Chap 13 (pp 313-338)
(d) In case where Z is alkenyloxy group: "Preparative Carbohydrate Chemistry", Marcel Dekker, Inc., 1997, Chap 14 (pp 339-356) and "Carbohydrates in Chemistry and Biology", Wiley-VCH, 2000, Vol. 1, Chap 6 (pp 135-154)
(e) In case where Z is a group —P(O$R^1$)$_3$; "Carbohydrates in Chemistry and Biology", Wiley-VCH, 2000, Vol. 1, Chap 5 (pp 117-134)
(f) In case where Z is a group —PO(O$R^1$)$_3$; J. Chem. Soc., Chem. Commun. 1989, 685 and J. Am. Chem. Soc. 2001, 123, 9545

The process of the invention is capable of inhibiting the formation of the o-ester by-product resulting from the conventional glycosilation reaction of pyranose compounds of 1,2-trans form, affording 1,2-transglycoside compounds with high selectivity.

FIG. 1 schematically shows the advantage of the preparation process of the invention

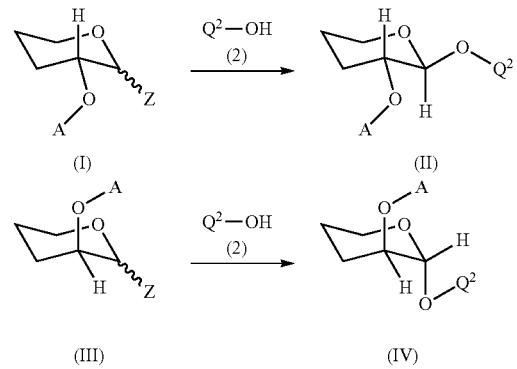

FIG. 1 wherein A, $Q^2$ and Z are as defined above.

With reference to FIG. 1 showing the present invention, an alcohol compound of the formula (2) is caused to act on a 2-phosphonoylpyranose compound (1 or III) in which the hydroxyl group at the 2-position is protected with a specified phosphoric acid ester serving as a protective group A to produce an o-glycoside compound (II or IV) wherein the stereoarrangement of the o-glycoside linkage at the 1-position of the pyranose ring and the protected hydroxyl group at the 2-position is made to have a trans form with high selectivity. Furthermore the process ensures the selectivity of the stereoarrangement without being influenced greatly by the kind of the alcohol compound used.

A glycoside linkage can be formed anew by causing an alcohol compound to act on 2-phosphonoyl-1,2-transglycoside compound of the formula (3a) which is included among the 2-phosphonoylk-1,2-transglycoside compounds of the formula (3) prepared by the present process. When the alcohol compound to be used is an alcohol compound of the formula (2a), it becomes possible to form another glycoside linkage, with the result that the oligosaccharide can be lengthened as desired in accordance with the number of repetitions $$Q^{1a}\text{-O-}Q^{2a} \qquad (3a)$$

wherein $Q^{1a}$ and $Q^{2a}$ are as defined above $$Q^{2a}\text{-OH} \qquad (2a)$$

wherein $Q^{2a}$ is as defined above.

The 2-phosphonoyl-1,2-transglycoside compound of the formula (3) and the 2-phosphonoyl-1,2-transglycoside compound of the formula (3a) thus obtained are novel compounds which have not been disclosed in literature.

The protective group A for the 2-position hydroxyl group is removable easily from the glycoside compounds obtained.

For example, as represented by Reaction Formula-3, a base is caused to act on the 2-phosphonoyl-1,2-transglucoside compound of the formula (3), whereby the group A is removed to give a 1,2-transglycoside compound of the formula (4).

Reaction Formula-3

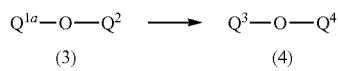

wherein $Q^{1a}$, $Q^2$, $Q^3$ and $Q^4$ are as defined above.

The base to be used is, for example, sodium methoxide, sodium ethoxide, potassium tert-butoxide or like alkali metal alkoxide, or sodium hydroxide, potassium hydroxide or like alkali metal hydroxide.

These bases can be used singly, or at least two of them are usable in combination. The base is used in an amount of 1 to 10 equivalents, preferably 2.0 to 5.0 equivalents, based on the compound (3).

The reaction is conducted in a solvent. The solvent to be used is methanol, ethanol, isopropanol or like alcohol, water, or a solvent mixture of such solvents, or a solvent mixture of water or alcohol and tetrahydrofuran or dioxane.

These solvents are used in an amount of about 1 to about 100 liters, preferably about S to about 20 liters, per kg of the compound (3).

The reaction temperature can be set to a desired value in the range of 0° C. to the boiling point of the solvent, and is usually preferably room temperature to about 60° C. Although not limited particularly, the reaction time is usually about 0.5 to about 10 hours to achieve a satisfactory result

BEST MODE OF CARRYING OUT THE INVENTION

The present invention will be described below in greater detail with reference to examples. However, the invention is not limited to these examples. The parts are by weight unless otherwise specified. With reference to the table, SPh stands for thiophenyl Bn for benzyl, TBS for tert-butyldimethylsilyl, c-Hex for cyclohexyl, Ph for phenyl and TCPN for tetrachlorophthaloyl.

Reference Example 1

Preparation of Phosphoric Acid Halide A-X³
(A=A-2, X³=Cl)

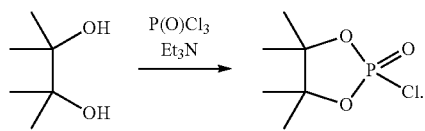

A dichloromethane solution (40.0 ml) of 2,3-dimethyl-2,3-butanediol (2.4 g, 20.0 mmols) was added to a solution of phosphorus oxychloride (3.7 g, 24.0 mmols) and triethylamine (4.9 g, 48.0 mmols) at room temperature, and the mixture was stirred at the same temperature for 2 hours. The resulting reaction mixture was concentrated in a vacuum, giving a crude product, which was purified by sublimation to give the desired product in the form of a white solid in a yield of 80%.

$^1$H-NMR (400 MHz, CDCl$_3$) 1.51 (s, 6H), 1.53 (s, 6H).

Example 1

Phenyl 3,4,6-tri-O-benzyl-2-O-(1,1,2,2-tetramethyl-dimethylene phosphonoyl)-β-D-thioglucopyranoside

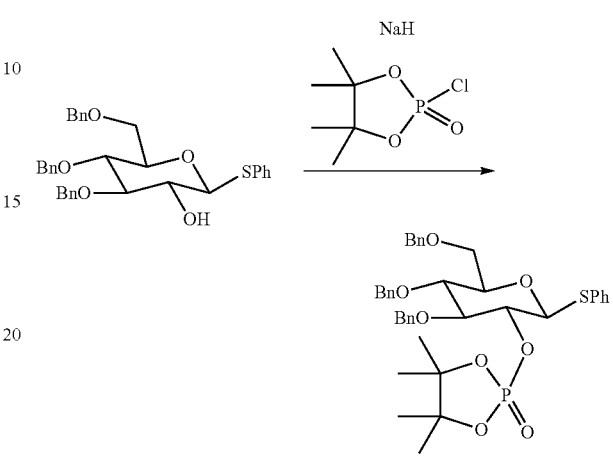

To 60-72% solution of sodium hydride (80.0 mg, 2.0 mmols) was added at room temperature a solution of 3,4,6-tri-O-benzyl-β-D-thioglucopyranosid (542.7 mg, 1.0 mmol) in 2.0 ml of THF. Thirty minutes later, 2,3-dimethyl-2,3-butylene phosphorochloridate (297.9 mg, 1.5 mmols) was added to the reaction mixture. The reaction was terminated with saturated aqueous solution of sodium bicarbonate 3.5 hours later. The organic layer was separated off, the aqueous layer was subjected to extraction with ethyl acetate, and the extraction organic layers were all combined together and washed with saturated saline solution. The washed layer was dried over magnesium sulfate and thereafter treated by filtration. The organic solvent was removed from the filtrate in a vacuum by a rotary evaporator to obtain a crude product.

The desired product (456.5 mg) was obtained from the crude product by flash chromatography (silica gel 37 g; elution with 40% ethyl acetate in hexane).

Yield: 65%

Properties: amorphous powder $^1$H NMR (400 MHz, CDCl$_3$): 1.35 (s, 3H), 1.39 (s, 3H), 1.42 (s, 3H), 1.49 (s, 3H), 3.50-3.57 (m, 1H), 3.61 (t, J=9.2 Hz, 1H), 3.65-3.73 (m, 2H), 3.77 (dd, J=11.0, 1.4 Hz, 1H), 4.42-4.52 (m, 1H), 4.51 (d, J=12.0 Hz, 1H), 4.53 (d, J=12.8 Hz, 1H), 4.56 (d, J=12.0 Hz, 1H), 4.66 (d, J=10.0 Hz, 1H), 4.76 (d, J=10.8 Hz, 2H), 4.96 (d, J=10.8 Hz, 1H), 7.14-7.20 (m, 2H), 7.22-7.35 (m, 14H), 7.38-7.43 (m, 2H), 7.60-7.66 (m, 2H).

$^{13}$C NMR (100 MHz, CDCl$_3$): 23.67 (CH$_3$, J$_{CP}$=4.6 Hz), 23.72 (CH$_3$, J$_{CP}$=54 Hz), 24.02 (CH$_3$, J$_{CP}$=5.3 Hz), 24.15 (CH$_3$, J$_{CP}$=5.4 Hz), 68.89 (CH$_2$), 73.42 (CH$_2$), 74.92 (CH$_2$), 75.39 (CH$_2$), 77.55 (CH), 77.95 (CH, J$_{CP}$=6.9 Hz), 79.37 (CH), 84.94 (CH, J$_{CP}$=3.1 Hz), 86.82 (CH, J$_{CP}$=3.8 Hz), 88.20 (C), 88.38 (C), 127.51 (CH), 127.54 (CH), 127.62 (CH, 2C), 127.75 (CH, 2C), 127.84 (CH, 2C), 128.11 (CH, 2C), 128.17 (CH, 2C), 128.30 (CH, 2C), 128.36 (CH, 2C), 128.74 (CH, 2C), 132.86 (CH, 2C), 133.09 (C), 137.92 (C), 138.07 (C), 138.18 (C).

In the same manner, Examples 2 to 10 were conducted.

Example 2

Phenyl 3,4,6-tri-O-benzyl-2-O-(diphenoxy phosphonoyl)-β-D-thioglucopyranoside

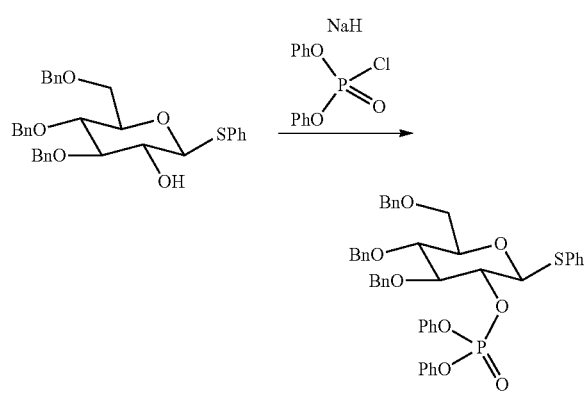

Yield: 57%
Properties: white powder
¹H-NMR (400 MHz, CDCl₃): 3.53-3.60 (m, 1H), 3.66-3.85 (m, 4H), 4.52 (d, J=12.0 Hz, 1H), 4.55 (d, J=11.6 Hz, 1H), 4.58 (d, J=12.0 Hz, 1H), 4.54-4.66 (m, 1H), 4.73 (d, J=8.8 Hz, 1H), 4.73 (d, J=9.6 Hz, 1H), 4.83 (d, J=10.4 Hz, 1H), 4.90 (d, J=10.4 Hz, 1H), 7.00-7.53 (m, 30H).

Example 3

Phenyl 3,4,6-tri-O-benzyl-2-O-(trimethylene phosphonoyl)-β-D-thioglucopyranoside

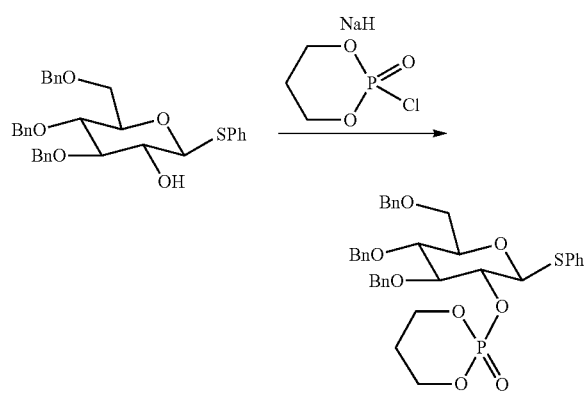

Yield: 52%
Properties: amorphous powder
¹H NMR (400 MHz, CDCl₃): 1.73-1.87 (m, 1H), 1.96-2.11 (m, 1H), 3.57-3.63 (m, 1H), 3.66 (dd, J=9.8, 8.6 Hz, 1H), 3.72 (dd, J=11.0, 4.6 Hz, 1H), 3.76-3.83 (m, 1H), 3.86 (t, J=8.6 Hz, 1H), 4.32-4.23 (m, 5H), 4.54 (d, J=12.4 Hz, 1H), 4.57 (d, J=11.2 Hz, 1H), 4.59 (d, J=10.8 Hz, 1H), 4.78 (d, J=11.2 Hz, 1H), 4.79 (d, J=10.0 Hz, 1H), 4.82 (d, J=10.4 Hz, 1H), 4.96 (d, J=10.4 Hz, 1H), 7.17-7.22 (m, 2H), 7.22-7.39 (m, 14H), 7.40-7.45 (m, 2H), 7.61-7.67 (m, 2H).
¹³C NMR (100 MHz, CDCl₃): 25.86 (CH₂, $J_{CP}$=6.9 Hz), 68.41 (CH₂, $J_{CP}$=8.4 Hz), 68.48 (CH₂, $J_{CP}$=68 Hz), 68.82 (CH₂), 73.39 (CH₂), 74.87 (CH₂), 75.34 (CH₂), 77.65 (CH, $J_{CP}$=3.8 Hz), 77.66 (CH), 79.31 (CH), 84.63 (CH, $J_{CP}$=1.5 Hz), 85.94 (CH, $J_{CP}$=4.6 Hz), 127.53 (CH), 127.58 (CH, 2C), 127.60 (CH), 127.78 (CH), 127.83 (CH, 2C), 127.94 (CH), 128.07 (CH, 2C), 128.27 (CH, 2C), 128.31 (CH, 2C), 128.38 (CH, 2C), 128.85 (CH, 2C), 132.19 (C), 132.91 (CH, 2C), 137.83 (C), 137.97 (C), 138.15 (C).
HRMS (FAB) m/z: Calcd for $C_{36}H_{40}O_8PS$ (M+H)⁺, 663.2182. Found 663.2194.

Example 4

Phenyl 3,4,6-tri-O-benzyl-2-O-(2-methyltrimethylene phosphonoyl)-β-D-thioglucopyranoside

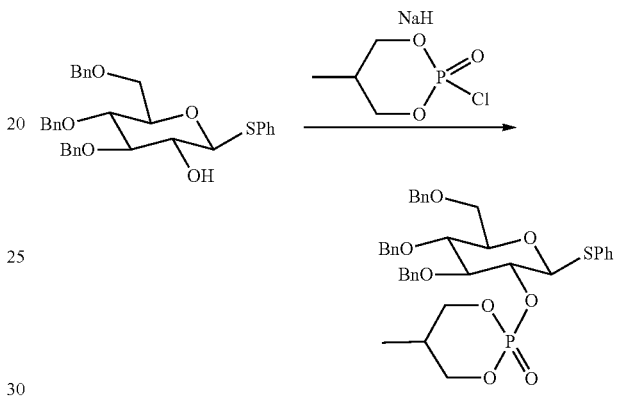

Yield: 55% (diastereo ratio 79:21)
Properties: white powder
HRMS (FAB) m/z: Calcd for $C_{37}H_{42}O_8PS$ (M+H)⁺, 677.2338. Found 677.2346.

Example 5

Phenyl 3,4,6-tri-O-benzyl-2-O-[(1R,3R)-1,3-dimethyltrimethylene phosphonoyl]-β-D-thioglucopyranoside

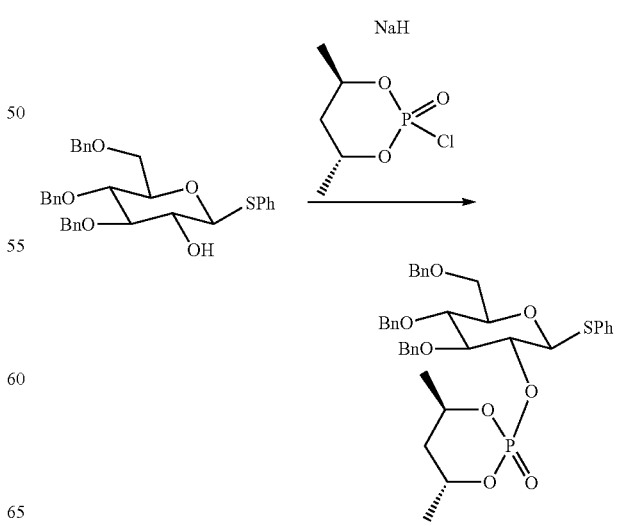

Yield: 51%

Properties: amorphous powder $^1$H NMR (400 MHz, CDCl$_3$): 1.31 (dd, J=6.4, 1.6 Hz, 3H), 1.45 (dd, J=6.6, 1.0 Hz, 1H), 1.80-1.88 (m, 1H), 1.93-2.02 (m, 1H), 3.52-3.60 (m, 1H), 3.61 (t, J=9.2 Hz, 1H), 3.68 (dd, J=11.0, 4.6 Hz, 1H), 3.76 (dd, J=10.8, 1.6 Hz, 1H), 3.84 (t, J=8.6 Hz, 1H), 4.38-4.50 (m, 1H), 4.51 (d, J=12.0 Hz, 1H), 4.53 (d, J=11.2 Hz, 1H), 4.57 (d, J=11.6 Hz, 1H), 4.67-4.77 (m, 1H), 4.74 (d, J=10.4 Hz, 2H), 4.79 (d, J=10.4 Hz, 1H), 4.78-4.90 (m, 1H), 4.94 (d, J=10.8 Hz, 1H), 7.14-7.18 (m, 2H), 7.22-7.34 (m, 16H), 7.38-7.43 (m, 2H), 7.59-7.64 (m, 2H).

$^{13}$C NMR (100 MHz, CDCl$_3$): 21.26 (CH$_3$, J$_{CP}$=3.8 Hz), 21.72 (CH$_3$, J$_{CP}$=6.9 Hz), 37.71 (CH$_2$, J$_{CP}$=6.1 Hz), 68.89 (CH$_2$), 72.83 (CH, J$_{CP}$=6.9 Hz), 73.39 (CH$_2$), 74.01 (CH, J$_{CP}$=6.1 Hz), 74.90 (CH$_2$), 75.24 (CH$_2$), 77.62 (CH), 78.02 (CH, J$_{CP}$=6.9 Hz), 79.24 (CH), 84.79 (CH, J$_{CP}$=2.3 Hz), 86.36 (CH, J$_{CP}$=3.8 Hz), 127.52 (CH, 2C), 127.60 (CH, 2C), 127.76 (CH, 2C), 127.86 (CH, 4C), 128.20 (CH, 2C), 128.30 (CH, 2C), 128.36 (CH, 2C), 128.80 (CH, 2C), 132.72 (CH, 2C), 132.82 (C), 137.88 (C), 138.13 (C), 138.19 (C).

HRMS (FAB) m/z: Calcd for C$_{38}$H$_{44}$O$_8$PS (M+H)$^+$, 691.2495. Found 691.2491.

Example 6

Phenyl 3,4,6-tri-O-benzyl-2-O-[(1S,3S)-1,3-dimethyltrimethylene phosphonoyl]-β-D-thioglucopyranoside

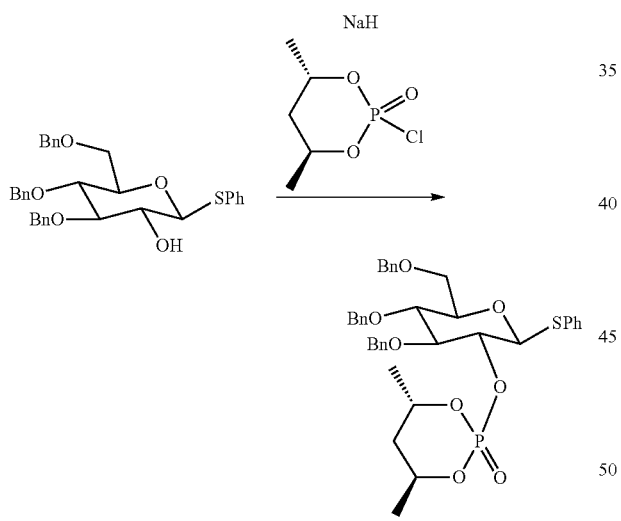

Yield: 48%

Properties: amorphous powder $^1$H NMR (400 MHz, CDCl$_3$): 1.37 (dd, J=6.4, 0.8 Hz, 3H), 1.45 (dd, J=6.4, 2.0 Hz, 3H), 1.80-1.88 (m, 1H), 1.96-2.03 (m, 1H), 3.52-3.64 (m, 2H), 3.67 (dd, J=11.0, 4.6 Hz, 1H), 3.73 (t, J=8.4 Hz, 1H), 3.76 (dd, J=11.0, 1.8 Hz, 1H), 4.43 (ddd, J=11.4, 9.4, 9.0 Hz, 1H), 4.51 (d, J=12.0 Hz, 1H), 4.52 (d, J=10.8 Hz, 1H), 4.56 (d, J=12.0 Hz, 1H), 4.69 (d, J=9.6 Hz, 1H), 4.75 (d, J=10.8 Hz, 2H), 4.71-4.84 (m, 2H), 4.99 (d, i=10.8 Hz, 1H), 7.13-7.18 (m, 2H), 7.21-7.36 (m, 14H), 7.39-7.44 (m, 2H), 7.58-7.64 (m, 2H).

$^{13}$C NMR (100 MHz, CDCl$_3$): 21.30 (CH$_3$, J$_{CP}$=5.4 Hz), 21.86 (CH$_3$, J$_{CP}$=7.6 Hz), 37.79 (CH$_2$, J$_{CP}$=6.9 Hz), 68.93 (CH$_2$), 72.54 (CH, J$_{CP}$=6.1 Hz), 73.39 (CH$_2$), 74.04 (CH, J$_{CP}$=6.9 Hz), 74.93 (CH$_2$), 75.46 (CH$_2$), 77.44 (CH), 77.56 (CH, J$_{CP}$=6.8 Hz), 79.36 (CH), 85.11 (CH, J$_{CP}$=2.3 Hz), 86.11 (CH, J$_{CP}$=4.6 Hz), 127.52 (CH), 127.54 (CH), 127.58 (CH, 2C), 127.76 (CH), 127.83 (CH), 127.88 (CH, 2C), 128.12 (CH, 2C), 128.22 (CH, 2C), 128.30 (CH, 2C), 128.36 (CH, 2C), 128.83 (CH, 2C), 132.47 (C), 132.79 (CH, 2C), 137.89 (C), 138.08 (C), 138.18 (C).

HRMS (FAB) m/z: Calcd for C$_{38}$H$_{44}$O$_8$PS (M+H)$^+$, 691.2495. Found 691.2515.

Example 7

Phenyl 3,4,6-tri-O-benzyl-2-O-(1,1-dimethyltrimethylene phosphonoyl)-β-D-thioglucopyranoside

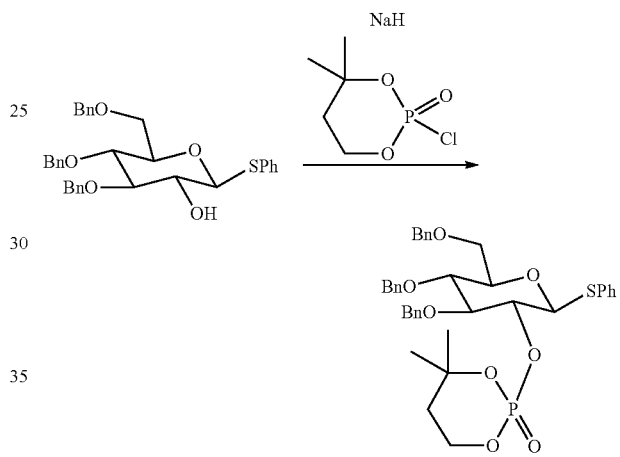

Yield: 54% (diastereo ratio 69:31)

Properties: amorphous powder

HRMS (FAB) m/z: Calcd for C$_{38}$H$_{44}$O$_8$PS (M+H)$^+$, 691.2495. Found 691.2483.

Example 8

Phenyl 3,4,6-tri-O-benzyl-2-O-(1,1,3,3-tetramethyltrimethylene phosphonoyl)-β-D-thio-glucopyranoside

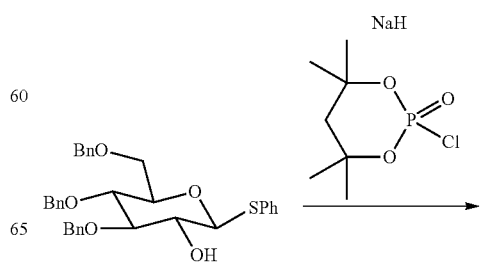

-continued

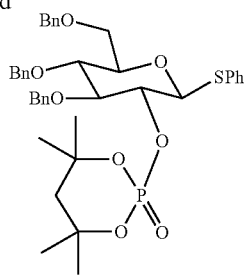

Yield: 91%
Properties: amorphous powder
$^1$H NMR (400 MHz, CDCl$_3$): 1.36 (s, 3H), 1.48 (s, 3H), 1.49 (s, 3H), 1.57 (s, 3H), 1.97 (dd, J=14.8, 0.8 Hz, 1H), 2.04 (dd, J=14.8, 1.2 Hz, 1H), 3.55 (ddd, J=9.7, 4.9, 1.7 Hz, 1H), 3.61 (t, J=9.2 Hz, 1H), 3.64-3.76 (m, 3H), 4.45-4.50 (m, 1H), 4.52 (d, J=10.4 Hz, 1H), 4.52 (d, J=10.8 Hz, 1H), 4.57 (d, J=12.0 Hz, 1H), 4.68 (d, J=10.0 Hz, 1H), 4.74 (d, J=11.2 Hz, 1H), 4.77 (d, J=10.0 Hz, 1H), 5.01 (d, J=10.4 Hz, 1H), 7.15-7.17 (m, 2H), 7.23-7.33 (m, 14H), 7.42-7.44 (m, 2H), 7.61-7.63 (m, 2H).
$^{13}$C NMR (100 MHz, CDCl$_3$): 30.53 (d, J$_{CP}$=3.8 Hz, CH$_3$), 30.56 (d, J$_{CP}$=3.8 Hz, CH$_3$), 30.69 (d, J$_{CP}$=5.3 Hz, CH$_3$), 31.10 (d, J$_{CP}$=5.4 Hz, CH$_3$), 47.30 (d, J$_{CP}$=6.8 Hz, CH$_2$), 68.97 (CH$_2$), 73.38 (CH$_2$), 74.86 (CH$_2$), 75.11 (CH$_2$), 77.56 (CH), 77.73 (d, J$_{CP}$=6.8 Hz, CH), 79.25 (CH), 82.13 (d, J$_{CP}$=6.1 Hz, C), 82.19 (d, J$_{CP}$=6.1 Hz, C), 85.11 (d, J$_{CP}$=2.3 Hz, CH), 86.70 (d, J$_{CP}$=54.6 Hz, CH), 127.36 (CH), 127.48 (CH), 127.60 (CH, 3C), 127.72 (CH, 2C), 127.79 (CH, 2C), 127.88 (CH, 2C), 128.10 (CH, 2C), 128.28 (CH, 2C), 128.33 (CH, 2C), 128.73 (CH, 2C), 132.56 (CH, 2C), 133.26 (C), 137.91 (C), 138.20 (C), 138.31 (C).
HRMS (FAB) m/z: Calcd for C$_{40}$H$_{48}$O$_9$PS (M+H)$^+$, 719.2808. Found 719.2810.

Example 9

Phenyl 3,4,6-tri-O-benzyl-2-O-(2,2-dimethyltrimethylene phosphonoyl)-β-D-thioglucopyranoside

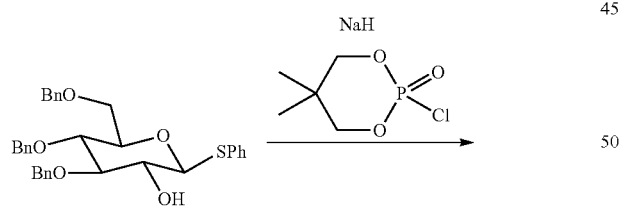

Yield: 94%
Properties: amorphous powder
$^1$H NMR (400 MHz, CDCl$_3$): 0.90 (s, 3H), 1.24 (s, 3H), 3.53-3.60 (m, 1H), 3.62 (t, J=9.2 Hz, 1H), 3.69 (dd, J=11.0, 4.6 Hz, 1H), 3.76 (dd, J=10.8, 2.0 Hz, 1H), 3.83 (t, J=8.8 Hz, 1H), 3.86-4.02 (m, 2H), 4.12 (dd, J=10.8, 4.8 Hz, 1H), 4.19 (dd, J=11.2, 4.8 Hz, 1H), 4.40 (dt, J=12.8, 9.2 Hz, 1H), 4.51 (d, J=12.0 Hz, 1H), 4.54 (d, J=12.8 Hz, 1H), 4.57 (d, J=12.0 Hz, 1H), 4.75 (d, J=12.8 Hz, 1H), 4.75 (d, J=9.6 Hz, 1H), 4.78 (d, J=10.0 Hz, 1H), 4.92 (d, J=10.4 Hz, 1H), 7.14-7.19 (m, 2H), 7.22-7.36 (m, 14H), 7.36-7.41 (m, 2H), 7.58-7.63 (m, 2H).

Example 10

Phenyl 3,4,6-tri-O-benzyl-2-O-(benzylidene phosphoronoyl)-β-D-thioglucopyranoside

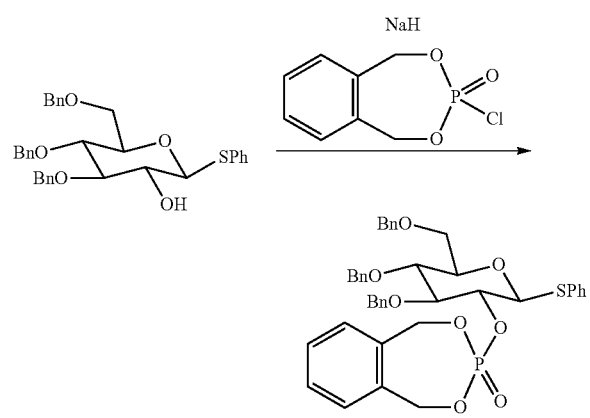

Yield: 840
Properties: white powder
$^1$H NMR (400 MHz, CDCl$_3$): 3.55 (ddd, J=9.6, 4.6, 1.8 Hz, 1H), 3.64 (t, J=9.4 Hz, 1H), 3.70 (dd, J=11.0, 4.6 Hz, 1H), 3.73-3.82 (m, 2H), 4.44-4.54 (m, 1H), 4.51 (d, J=12.0 Hz, 1H), 4.54 (d, J=11.6 Hz, 1H), 4.57 (d, J=12.0 Hz, 1H), 4.72 (d, J=9.6 Hz, 1H), 4.75 (d, J=10.6 Hz, 1H), 4.82 (d, J=10.6 Hz, 1H), 4.92-5.05 (m, 2H), 5.19-5.36 (m, 3H), 7.13-7.20 (m, 2H), 7.20-7.37 (m, 18H), 7.38-7.43 (m, 2H), 7.60-7.65 (m, 2H).

Example 11

Cyclohexyl 3,4,6-tri-O-benzyl-2-O-(1,1,2,2-tetramethyldimethylene phosphornoyl)-β-D-glucopyranoside

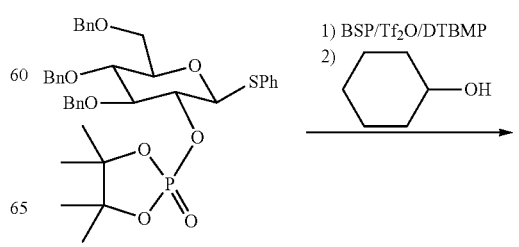

-continued

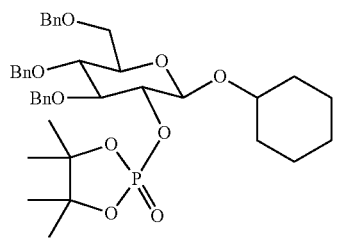

Tf₂O (33.9 mg, 0.12 mmol) was added at 60° C. to a mixture solution of the 2-phosphonoylphenylglucoside compound (63.9 mg, 0.09 mmol) prepared in Example 1, BSP (20.9 mg, 0.10 mmol), DTBMP (39.0 mg, 0.18 mmol) and 0.9 ml of dichloromethane containing about 90 mg of molecular sieves 4A. Cyclohexanol (13.0 mg, 0.14 mmol) was added to the solution 30 minutes later. Et₃N (0.09 ml) was further added to the mixture 30 minutes later to quench the reaction. The reaction mixture was warmed up to room temperature and neutralized with saturated aqueous sodium bicarbonate solution. The organic layer was separated off, the aqueous layer portion was subjected to extraction with ethyl acetate three times, and the extraction organic layers were all combined together and washed with saturated saline solution. The washed layer was thereafter dried over magnesium sulfate and subsequently filtered, and the filtrate was distilled in a vacuum to remove the organic solvent. The desired product was obtained from the residue by flash chromatography.

Yield: 87%

Properties: amorphous white powder

Isomers ratio α:β=<1:99

$^1$H NMR (400 MHz, CDCl₃): 1.17-1.30 (m, 2H), 1.37 (s, 3H), 1.38 (s, 3H), 1.44 (s, 3H), 1.45 (s, 3H), 1.44-1.58 (m, 4H), 1.72-1.82 (m, 2H), 1.86-1.99 (m, 2H), 3.47 (ddd, J=9.7, 5.3, 1.9 Hz 1H), 3.57 (t, J=9.2 hz, 1H), 3.60-3.71 (m, 2H), 3.69 (t, J=9.0 Hz, 1H), 3.73 (dd, J=10.8, 2.0 Hz, 1H), 4.40 (ddd, J=10.7, 9.1, 7.9 Hz 1H), 4.49 (d, J=8.0 Hz, 1H), 4.52 (d, J=11.2 Hz, 1H), 4.55 (d, J=12.0 Hz, 1H), 4.59 (d, J=12.0 Hz, 1H), 4.73 (d, J=10.8 Hz, 1H), 4.78 (d, J=10.8 Hz, 1H), 4.94 (d, J=10.4 Hz, 1H), 7.12-7.19 (m, 2H), 7.23-7.35 (m, 11H), 7.38-7.43 (m, 2H).

$^{13}$C NMR (100 MHz, CDCl₃): 23.70 (CH₃, $J_{CP}$=3.1 Hz), 23.76 (CH₂, $J_{CP}$=3.0 Hz), 23.81 (CH₂), 23.91 (CH₂), 24.09 (CH₃, $J_{CP}$=2.2 Hz), 24.15 (CH₃, $J_{CP}$=3.1 Hz), 25.64 (CH₂), 31.48 (CH₂), 33.37 (CH₂), 68.96 (CH₂), 73.36 (CH₂), 74.89 (CH₂), 75.04 (CH₂), 75.07 (CH), 77.75 (CH), 78.03 (CH), 79.55 (CH, $J_{CP}$=6.8 Hz), 83.56 (CH, $J_{CP}$=4.6 Hz), 87.88 (C, $J_{CP}$=9.2 Hz, 2C), 99.68 (CH, $J_{CP}$=3.1 Hz), 127.48 (CH), 127.53 (CH), 127.62 (CH, 2C), 127.69 (CH), 127.91 (CH, 2C), 128.20 (CH, 2C), 128.28 (CH, 2C), 128.30 (CH, 2C), 128.33 (CH, 2C), 137.99 (C), 138.21 (C), 138.24 (C).

In the same manner, Examples 12 to 22 were conducted.

Example 12

Methyl 3,4,6-tri-O-benzyl-2-O-(diphenoxy phosphonoyl)-β-D-glucopyranoside

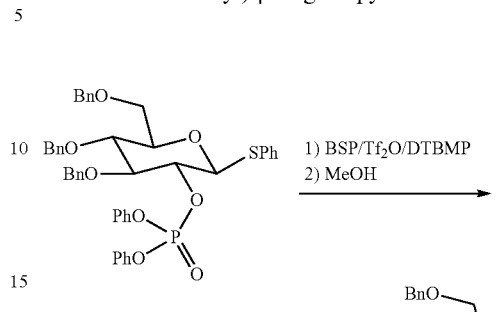

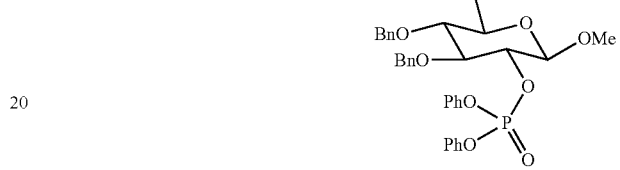

Yield: 88%

Properties: amorphous white powder

Isomers ratio α:β=<1:99

$^1$H NMR (400 MHz, CDCl₃): 3.35 (s, 3H), 3.50 (ddd, J=9.6, 4.4, 2.0 Hz, 1H), 3.65-3.80 (m, 4H), 4.38 (d, J=7.6 Hz, 1H), 4.48-4.57 (m, 3H), 4.61 (d, J=12.4 Hz, 1H), 4.75 (d, J=10.8 Hz, 1H), 4.75 (d, J=12.4 Hz, 1H), 4.83 (d, J=10.8 Hz, 1H), 7.05-7.35 (m, 15H).

Example 13

Cyclohexyl 3,4,6-tri-O-benzyl-2-O-(trimethylene phosphonoyl)-β-D-glucopyranoside

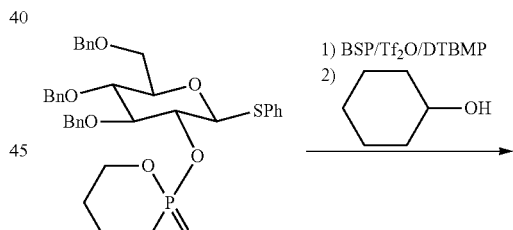

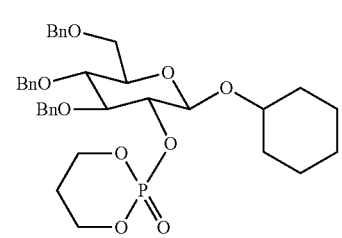

Yield: 84%

Properties: amorphous white powder

Isomers ratio α:β=<1:99

$^1$H NMR (400 MHz, CDCl₃): 1.12-1.59 (m, 6H), 1.70-1.82 (m, 3H), 1.91-2.04 (m, 2H), 2.12-2.26 (m, 1H), 3.51 (ddd, J=9.7, 5.1, 1.9 Hz 1H), 3.58-3.72 (m, 3H), 3.73 (dd, J=10.8, 2.0 Hz, 1H), 3.80 (t, J=9.0 Hz, 1H), 4.27 (ddd, J=11.8, 9.2, 7.8 Hz, 1H), 4.30-4.46 (m, 4H), 4.54 (d, J=11.2 Hz, 1H), 4.54 (d, J=12.4 Hz, 1H), 4.60 (d, J=12.4 Hz, 1H), 4.62 (d, J=7.6 Hz, 1H), 4.79 (d, J=10.0 Hz, 2H), 4.96 (d, J=10.4 Hz, 1H), 7.15-7.20 (m, 2H), 7.23-7.36 (m, 11H), 7.38-7.43 (m, 2H).

$^{13}$C NMR (100 MHz, CDCl$_3$): 24.03 (CH$_2$), 24.13 (CH$_2$), 25.55 (CH$_2$), 25.91 (CH$_2$, J$_{CP}$=6.9 Hz), 31.74 (CH$_2$), 33.64 (CH$_2$), 68.18 (CH$_2$, J$_{CP}$=6.9 Hz), 68.28 (CH$_2$, J$_{CP}$=7.7 Hz), 68.79 (CH$_2$), 73.34 (CH$_2$), 74.86 (CH$_2$), 74.89 (CH), 74.25 (CH$_2$), 77.89 (CH), 78.01 (CH), 79.49 (CH, J$_{CP}$=6.8 Hz), 83.50 (CH, J$_{CP}$=3.0 Hz), 99.28 (CH, J$_{CP}$=3.1 Hz), 127.52 (CH), 127.59 (CH, 3C), 127.75 (CH), 127.85 (CH, 2C), 128.17 (CH, 2C), 128.24 (CH, 2C), 128.30 (CH, 2C), 128.36 (CH, 2C), 137.87 (C), 138.12 (C), 138.14 (C).

HRMS (FAB) m/z: Calcd for C$_{36}$H$_{46}$O$_9$P (M+H)$^+$, 653.2879. Found 653.2886.

Example 14

Cyclohexyl 3,4,6-tri-O-benzyl-2-O-(2-methyltrimethylene phosphonoyl)-β-D-glucopyranoside

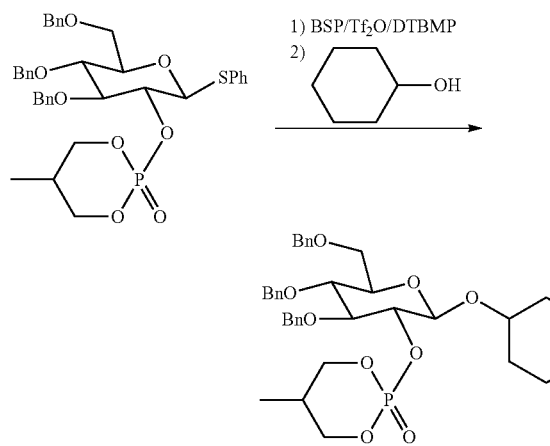

Yield: 82% (diastereo ratio 80:20)
Properties: amorphous white powder
Isomers ratio α:β=<1:99

Example 15

Cyclohexyl 3,4,6-tri-O-benzyl-2-O-[(1R,3R)-1,3-dimethyltrimethylene phosphornoyl]-β-D-glucopyranoside

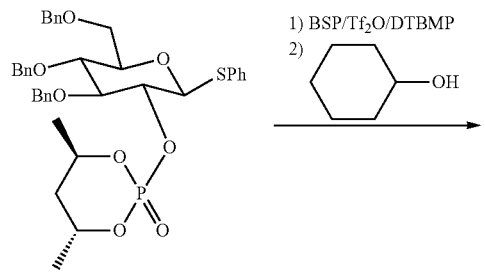

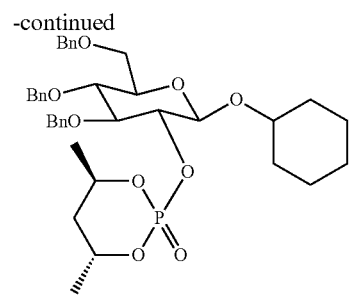

Yield: 65%
Properties: amorphous white powder
Isomers ratio α:β=0:100
$^1$H NMR (400 MHz, CDCl$_3$): 1.14-1.34 (m, 3H), 1.34-1.56 (m, 9H), 1.70-2.02 (m, 6H), 3.49 (ddd, J=9.9, 5.1, 1.9 Hz 1H), 3.59 (t, J=9.2 Hz, 1H), 3.61-3.72 (m, 2H), 3.73 (dd, J=10.8, 2.0 hz, 1H), 3.76 (t, J=8.8 Hz, 1H), 4.29 (ddd, J=12.0, 9.2, 8.0 Hz, 1H), 4.52 (d, J=10.8 Hz, 1H), 4.54 (d, J=12.0 Hz, 1H), 4.57 (d, J=10.0 Hz, 1H), 4.60 (d, J=12.0 Hz, 1H), 4.62-4.73 (m, 1H), 4.73-4.84 (m, 1H), 4.76 (d, J=10.8 Hz, 1H), 4.78 (d, J=11.2 Hz, 1H), 4.95 (d, J=10.4 Hz, 1H), 7.13-7.18 (m, 2H), 7.23-7.35 (m, 11H), 7.39-7.44 (m, 2H).

Example 16

Cyclohexyl 3,4,6-tri-O-benzyl-2-O-[(1S,3S)-1,3-dimethyltrimethylene phosphornoyl]-β-glucopyranoside

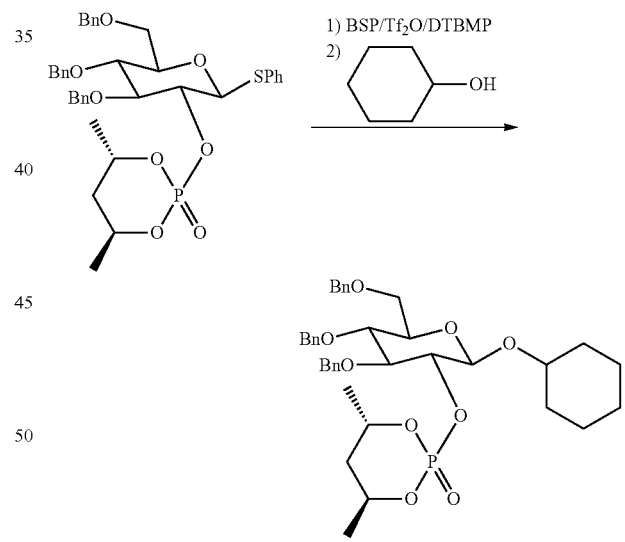

Yield: 81%
Properties: amorphous white powder
Isomers ratio α:β=<1:99
$^1$H NMR (400 MHz, CDCl$_3$): 1.13-1.34 (m, 3H), 1.34-1.58 (m, 9H), 1.72-2.03 (m, 6H), 3.49 (ddd, J=9.8, 5.0, 2.0 Hz, 1H), 3.59 (t, J=9.4 Hz, 1H), 3.62-3.71 (m, 2H), 3.73 (dd, J=11.2, 2.0 Hz, 1H), 3.73 (t, J=8.8 Hz, 1H), 4.29 (ddd, J=11.4, 9.2, 7.8 Hz, 1H), 4.52 (d, J=10.8 Hz, 1H), 4.54 (d, J=12.0 Hz, 1H), 4.56 (d, J=7.6 Hz, 1H), 4.59 (d, J=12.0 Hz, 1H), 4.62-4.72 (m, 1H), 4.72-4.84 (m, 1H), 4.75 (d, J=10.4 Hz, 1H), 4.79 (d, J=10.8 Hz, 1H), 4.98 (d, J=10.8 Hz, 1H), 7.14-7.20 (m, 2H), 7.22-7.36 (m, 11H), 7.39-7.45 (m, 2H).

$^{13}$C NMR (100 MHz, CDCl$_3$): 21.35 (CH$_3$, J$_{CP}$=5.3 Hz), 21.75 (CH$_3$, J$_{CP}$=6.8 Hz), 23.92 (CH$_2$), 24.05 (CH$_2$), 25.59 (CH$_2$), 31.68 (CH$_2$), 33.52 (CH$_2$), 37.83 (CH$_2$, J$_{CP}$=6.8 Hz), 68.87 (CH$_2$), 72.61 (CH, J$_{CP}$=6.8 Hz), 73.24 (CH, J$_{CP}$=6.1 Hz), 73.31 (CH$_2$), 74.86 (CH$_2$), 74.92 (CH), 75.28 (CH$_2$), 77.77 (CH, 2C), 79.45 (CH, J$_{CP}$=7.7 Hz), 83.80 (CH, J$_{CP}$=3.8 Hz), 99.45 (CH, J$_{CP}$=3.8 Hz), 127.46 (CH), 127.50 (CH), 127.57 (CH, 2C), 127.69 (CH), 127.85 (CH, 2C), 128.17 (CH, 4C), 128.25 (CH, 2C), 128.31 (CH, 2C), 137.91 (C), 138.15 (C), 138.18 (C).

Example 17

Cyclohexyl 3,4,6-tri-O-benzyl-2-O-(1,1-dimethyltrimethylene phosphonoyl)-β-D-glucopyranoside

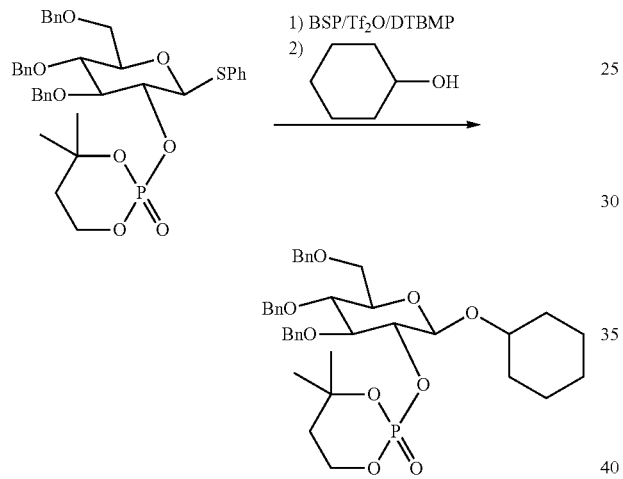

Yield: 40% (diastereo ratio 67:33)
Properties: amorphous white powder
Isomers ratio α:β<1:99

Example 18

Cyclohexyl 3,4,6-tri-O-benzyl-2-O-(1,1,3,3-tetramethyltrimethylene phosphonoyl)-β-D-glucopyranoside

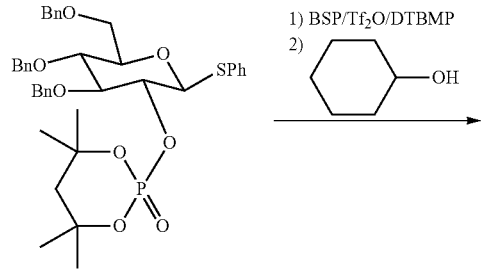

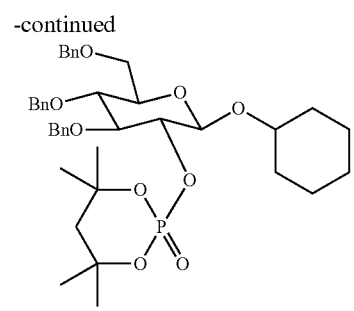

Yield: 34%
Properties: amorphous white powder
Isomers ratio α:β=<1:99

$^1$H NMR (400 MHz, CDCl$_3$): 1.16-2.12 (m, 24H), 3.49 (ddd, J=9.8, 5.2, 1.8 Hz, 1H), 3.57 (t, J=7.4 Hz, 1H), 3.58-3.77 (m, 4H), 4.34 (ddd, J=11.8, 9.0, 7.8 Hz, 1H), 4.48-4.62 (m, 4H), 4.75 (d, J=10.8 Hz, 1H), 4.78 (d, J=11.2 Hz, 1H), 4.99 (d, J=10.4 Hz, 1H), 7.14-7.20 (m, 2H), 7.22-7.35 (m, 11H), 7.40-7.45 (m, 2H).

Example 19

Cyclohexyl 3,4,6-tri-O-benzyl-2-O-(2,2-dimethyltrimethylene phosphonoyl)-β-D-glucopyranoside

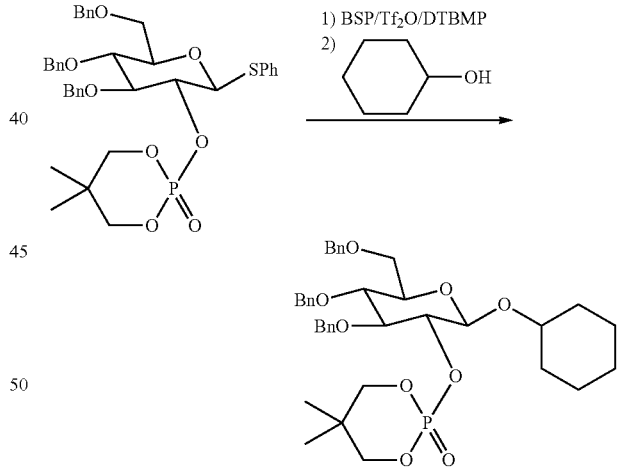

Yield: 77%
Properties: amorphous white powder
Isomers ratio α:β=0:100

$^1$H NMR (400 MHz, CDCl$_3$): 0.87 (s, 3H), 1.12-1.58 (m, 8H), 1.70-1.82 (m, 3H), 1.90-2.04 (m, 2H), 3.50 (ddd, J=9.6, 5.0, 1.8 Hz, 1H), 3.61 (t, J=9.4 Hz, 1H), 3.62-3.71 (m, 2H), 3.73 (dd, J=11.0, 1.8 Hz, 1H), 3.80 (t, J=9.0 Hz, 1H), 3.83-4.16 (m, 4H), 4.22-4.32 (m, 1H), 4.51-4.64 (m, 4H), 4.78 (d, J=10.4 Hz, 1H), 4.79 (d, J=11.2 Hz, 1H), 4.95 (d, J=10.4 Hz, 1H), 7.15-7.21 (m, 2H), 7.24-7.36 (m, 11H), 7.37-7.44 (m, 2H).

Example 20

Cyclohexyl 3,4,6-tri-O-benzyl-2-O-(benzylidene phosphoronoyl)-β-D-glucopyranoside

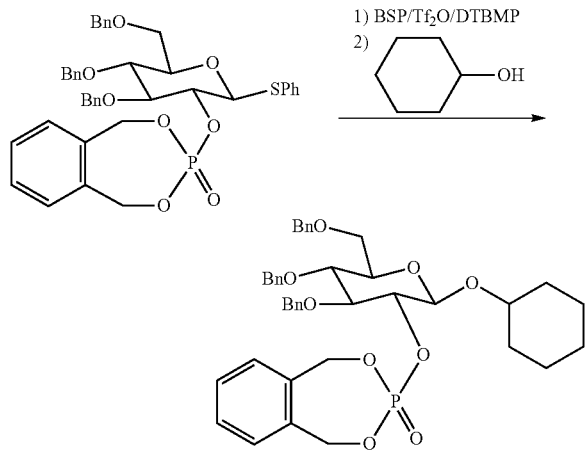

Yield: 87%
Properties: amorphous white powder
Isomers ratio α:β=<1:99
$^1$H NMR (400 MHz, CDCl$_3$): 1.17-1.68 (m, 5H), 1.71-1.84 (m, 3H), 1.90-2.02 (m, 2H), 3.49 (ddd, J=9.7, 5.1, 1.9 Hz 1H), 3.61 (t, J=9.2 Hz, 1H), 3.65 (dd, J=10.8, 5.2 Hz, 1H), 3.64-3.74 (m, 1H), 3.73 (dd, J=11.0, 1.8 Hz, 1H), 3.75 (t, J=9.0 Hz, 1H), 4.39 (dt, J=9.6, 7.9 Hz 1H), 4.50-4.62 (m, 4H), 4.78 (d, J=10.4 Hz, 2H), 4.97 (d, J=10.8 Hz, 1H), 5.04-5.32 (m, 4H), 7.14-7.68 (m, 19H).

Example 21

2,3,6-tri-O-benzyl-4-O-[3',4',6'-tri-O-benzyl-2'-O-(1,1,2,2-tetramethyldimethylene phosphonoyl)-β-D-glucopyranosyl]-β-D-thioglucopyranoside

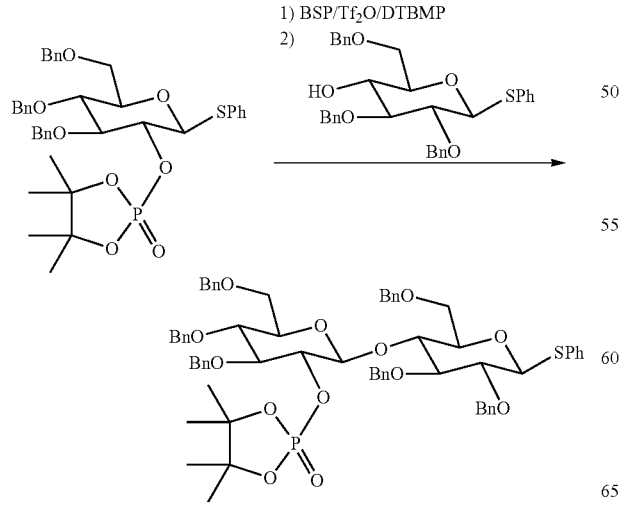

Yield: 56%
Properties: amorphous white powder
Isomers ratio α:β=9:91
$^1$H NMR (400 MHz, CDCl$_3$): 1.30 (s, 3H), 1.33 (s, 3H), 1.38 (s, 3H), 1.46 (s, 3H), 3.34 (br dd, J=9.6, 2.8 Hz, 1H), 3.42 (t, J=9.4 Hz, 1H), 3.47-3.56 (m, 3H), 3.60-3.80 (m, 4H), 3.95 (dd, J=11.2, 3.2 Hz, 1H), 4.08 (t, J=9.4 Hz, 1H), 4.33 (d, J=12.0 Hz, 1H), 4.37 (d, J=12.0 Hz, 1H), 4.37-4.49 (m, 1H), 4.50 (d, J=9.6 Hz, 1H), 4.50 (d, J=12.0 Hz, 1H), 4.58 (d, J=8.0 Hz, 1H), 4.63 (d, J=10.0 Hz, 1H), 4.68-4.76 (m, 6H), 4.87 (d, J=10.8 Hz, 1H), 5.13 (d, J=11.2 Hz, 1H), 7.10-7.16 (m, 4H), 7.18-7.35 (m, 27H), 7.36-7.40 (m, 2H), 7.54-7.60 (m, 2H).
$^{13}$C NMR (100 MHz, CDCl$_3$): 23.69 (CH$_3$, J$_{CP}$=6.9 Hz), 23.87 (CH$_3$, J$_{CP}$=6.9 Hz), 24.11 (CH$_3$, J$_{CP}$=3.0 Hz), 24.43 (CH$_3$, J$_{CP}$=3.8 Hz), 68.27 (CH$_2$), 68.77 (CH$_2$), 73.27 (CH$_2$), 73.47 (CH$_2$), 74.74 (CH$_2$), 75.13 (CH$_2$), 75.21 (CH$_2$), 75.30 (CH), 75.68 (CH$_2$), 76.04 (CH), 77.88 (CH), 78.83 (CH), 79.67 (CH, J$_{CP}$>=6.9 Hz), 79.79 (CH), 83.24 (CH, J$_{CP}$=3.8 Hz), 84.85 (CH), 87.09 (CH), 87.92 (C), 88.33 (C), 99.99 (CH, J$_{CP}$=3.9 Hz), 126.94 (CH), 127.21 (CH), 127.28 (CH), 127.34 (CH, 2C), 127.39 (CH), 127.42 (CH), 127.52 (CH), 127.55 (CH, 3C), 127.60 (CH, 2C), 127.85 (CH, 2C), 127.88 (CH, 6H), 128.06 (CH, 2C), 128.09 (CH, 4C), 128.18 (CH, 2C), 128.33 (CH, 2C), 128.67 (CH, 2C), 132.10 (CH, 2C), 133.34 (C), 137.88 (C), 137.97 (C), 138.05 (C), 138.13 (C)—, 138.14 (C), 138.99 (C).
HRMS (FAB) m/z: Calcd for C$_{66}$H$_{74}$O$_{13}$PS (M+H)$^+$, 1137.4588. Found 1137.4596.

Example 22

6-O-[6'-O-tert-butyldimethylsilyl-2'-O-(2,2-dimethyltrimethylene phosphonoyl)-3',4'-O-propyridene-β-D-glucopyranosyl]-2-O-(2,2-dimethyltrimethylene phosphonoyl)-3,4-O-propyridene-β-D-thioglucopyranoside

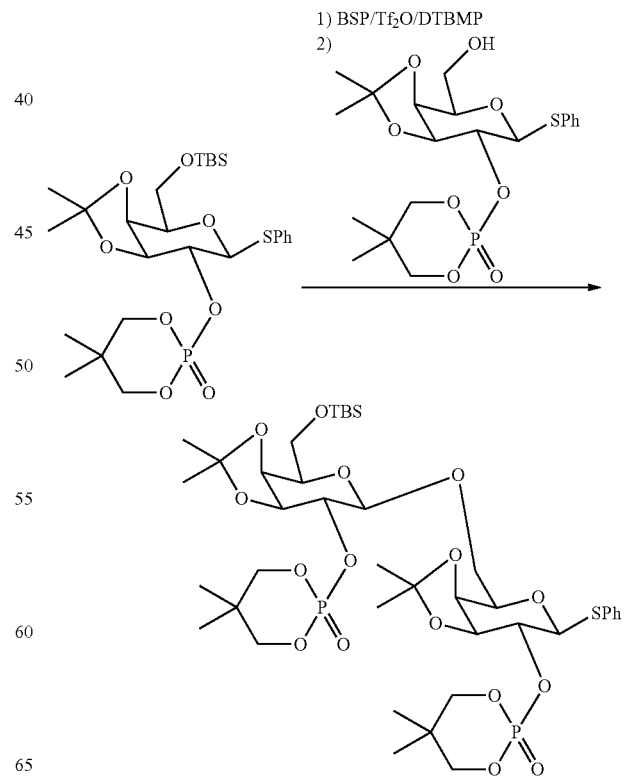

Yield: 67% (α:β=9:91)
Properties: amorphous white powder
Isomers ratio α:β=9:91
$^1$H NMR (400 MHz, CDCl$_3$): 0.07 (s, 6H), 0.77 (s, 3H), 0.89 (s, 3H), 0.89 (s, 9H), 1.19 (s, 3H), 1.25 (s, 3H), 1.34 (s, 3H), 1.35 (s, 3H), 1.51 (s, 3H), 1.56 (s, 3H), 3.70-4.28 (m, 17H), 4.32-4.49 (m, 3H), 4.61 (d, J=8.0 Hz, 1H), 4.86 (d, J=8.8 Hz, 1H), 7.22-7.36 (m, 3H), 7.52-7.58 (m, 2H).

Example 23

Deprotection

Deprotection of 2,3,6-tri-O-benzyl-4-O—[2'-O-acetyl-3',4',6'-tri-O-benzyl-β-D-glucopyranosyl]-β-D-thioglucopyranoside

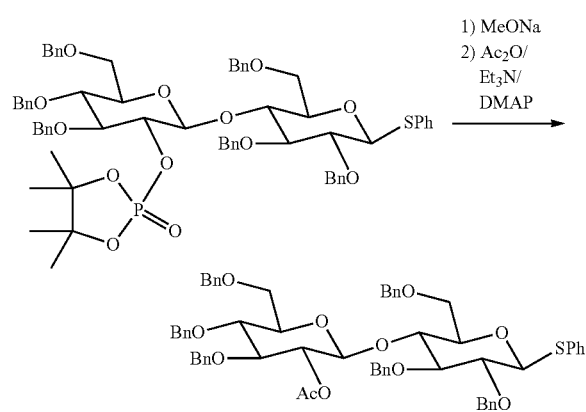

A solution of sodium (7.6 mg, 0.331 mmol) in 1 4-dioxane (0.50 ml) was added at room temperature to the 2-phosphonoyl-1,2-glycoside compound (20.5 mg, 0.018 mmol) prepared in Example 21, and the reaction mixture was neutralized with saturated aqueous solution of ammonium chloride 2 hours later. The organic layer was separated off, and the aqueous layer was subjected to extraction with ethyl acetate three times. The extracts and the organic layer were combined together, washed with saturated aqueous saline solution, dried over magnesium sulfate and concentrated in a vacuum to obtain a residue (20.5 mg). The residue was an alcohol compound resulting from the removal of the phosphonoyl group at the 2-position.

The residue (14.9 mg) was dissolved in methylene chloride (0.5 ml), and acetic anhydride (8.0 mg, 0.078 mmol), triethylamine (8.0 mg, 0.079 mmol) and DMAP (1.0 mg, 0.0082 mmol) were added to the solution at room temperature. The reaction mixture was neutralized with saturated aqueous solution of sodium hydrogencarbonate 2 hours later. The organic layer was separated off, and the aqueous layer was subjected to extraction with ethyl acetate three times. The extracts and the organic layer were combined together, washed with saturated aqueous saline solution, dried over magnesium sulfate and concentrated in a vacuum. The resulting residue was purified by flash chromatography (silica gel 1.0 g; elution with 30% ethyl acetate in hexane) to obtain a 2-acetoxyglycoside compound.

Yield: 90%
Properties: amorphous white powder
$^1$H NMR (400 MHz, CDCl$_3$): 1.82 (s, 3H), 3.20-3.27 (m, 1H), 3.30 (dt, J=9.9, 2.7 Hz, 1H), 3.35 (t, J=9.2 Hz, 1H), 3.39-3.48 (m, 2H), 3.32-3.72 (m, 5H), 3.87 (t, J=9.6 Hz, 1H), 4.22-4.32 (m, 2H), 4.44 (d, J=12.0 Hz, 2H), 4.47-4.73 (m, 9H), 4.88 (dd, J=9.0, 8.2 Hz, 1H), 5.03 (d, J=11.6 Hz, 1H), 7.04-7.28 (m, 33H), 7.43-7.49 (m, 2H).
$^{13}$C NMR (100 MHz, CDCl$_3$): 21.08 (CH$_3$), 68.07 (CH$_2$), 68.60 (CH$_2$), 73.23 (CH$_2$), 73.52 (CH$_2$), 73.65 (CH), 74.87 (CH$_2$), 75.07 (CH$_2$), 75.16 (CH), 75.30 (CH$_2$), 75.39 (CH$_2$), 76.62 (CH), 77.98 (CH), 78.98 (CH), 80.23 (CH), 83.01 (CH), 84.75 (CH), 87.40 (CH), 100.28 (CH), 127.00 (CH), 127.30 (CH, 2C), 127.39 (CH, 2C), 127.44 (CH, 2C), 127.57 (CH, 4C), 127.60 (CH), 127.65 (CH, 2C), 127.68 (CH), 127.79 (CH, 2C), 127.96 (CH, 2C), 128.04 (CH, 2C), 128.13 (CH, 4C), 128.26 (CH, 2C), 128.30 (CH, 4C), 128.72 (CH, 2C), 131.85 (CH, 2C), 133.52 (C), 137.73 (C), 137.87 (C), 137.90 (C), 137.96 (C), 138.06 (C), 138.94 (C), 169.09 (C=O).

INDUSTRIAL APPLICABILITY

According to the present invention, a specified phosphoric acid ester (phosphonoyl group) is used as a saccharide donor for glycosilation as a protective group for the hydroxyl group at the second position of a furanose compound or pyranose compound to thereby form a glycoside linkage of 1,2-trans form selectively, inhibit the formation of a by-product corresponding to an o-ester and make it possible to lengthen the saccharide chain as desired.

The invention claimed is:

1. A 2-phosphonoyl-1,2-transglycoside compound of the formula (3) comprising:

$$Q^{1a}\text{-O-}Q^2 \qquad (3)$$

wherein $Q^{1a}$ has the following structure:

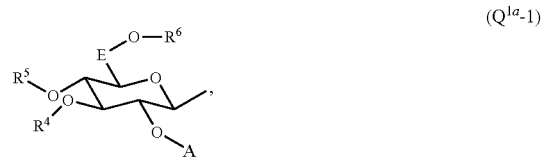
(Q$^{1a}$-1)

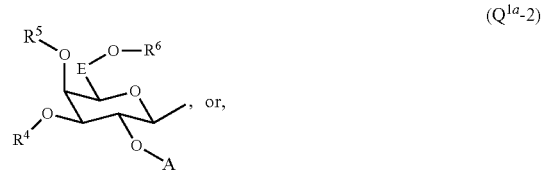
(Q$^{1a}$-2), or,

(Q$^{1a}$-3);

R$^4$, R$^5$ and R$^6$ are the same or different and are each a protective group for the saccharide hydroxyl group;

E is methylene or a carbonyl; and

A is

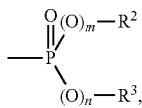
(A)

wherein $R^2$ and $R^3$ are the same or different and are each an alkyl group having 1 to 4 carbon atoms or an aryl group optionally substituted, or $R^2$ and $R^3$ are connected via an alkylene group having 2 to 4 carbon atoms, further wherein the alkylene group is optionally substituted with an alkyl group having 1 to 4 carbon atoms or optionally comprises an intervening phenylene, and m and n are each an integer of 0 or 1;

$Q^2$ is one of the following groups

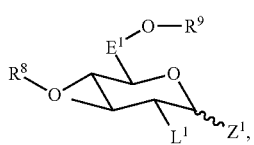
($Q^2$-1)

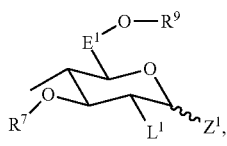
($Q^2$-2)

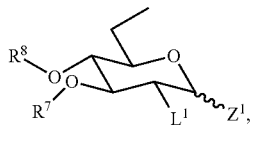
($Q^2$-3)

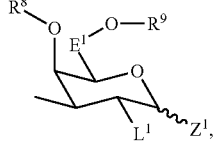
($Q^2$-4)

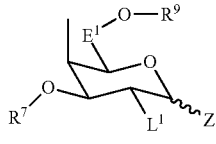
($Q^2$-5)

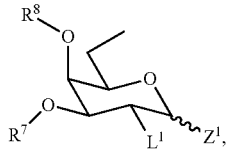
($Q^2$-6)

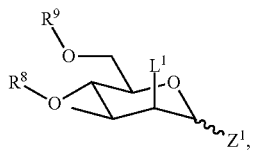
($Q^2$-7)

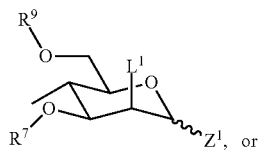
($Q^2$-8)

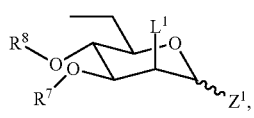
($Q^2$-9)

wherein $L^1$ is a group —$OA^1$, —OG or —$N(J^1)(J^2)$; G is a protective group for the saccharide hydroxyl, and $J^1$ and $J^2$ are each a hydrogen atom or a protective group for the amino; $A^1$ is

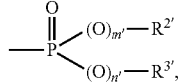
($A^1$)

$R^{2'}$ and $R^{3'}$ are the same or different and are each alkyl comprising 1 to 4 carbon atoms or aryl optionally substituted, or $R^{2'}$ and $R^{3'}$ are combined with each other to form an alkylene having 2 or 4 carbon atoms, further wherein the alkylene is optionally substituted with alkyl having 1 to 4 carbon atoms, or optionally comprises an intervening phenylene; m' and n' are each an integer of 0 or 1;

$Z^1$ is a group —S—$R^{1'}$, a group —SO—$R^{1'}$, a group —Se—$R^{1'}$, a group —O—C(=NH)$CX'_3$, a halogen atom, an alkoxyl, an alkenyloxy, a group —P$(OR^{1'})_3$, a group —PO$(OR^{1'})_3$ or —$OG^1$; $R^{1'}$ is an alkyl comprising 1 to 20 carbon atoms, an aryl optionally substituted or a heteroaromatic group; X' is a halogen atom; $G^1$ is a protective group for the saccharide hydroxyl;

$R^7$, $R^8$ and $R^9$ are the same or different and are each a protective group for the saccharide hydroxyl group; and $E^1$ is methylene or a carbonyl.

2. A 2-phosphonoyl-1,2-transglycoside compound of the formula (3a) comprising:

$$Q^{1a}\text{-}O\text{-}Q^{2a} \quad (3a)$$

wherein $Q^{1a}$ has the following structure:

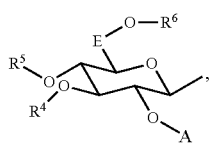
($Q^{1a}$-1)

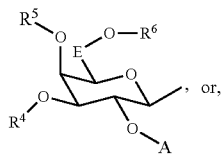
($Q^{1a}$-2)

(Q$^{1a}$-3)

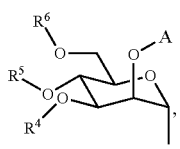

R$^4$, R$^5$ and R$^6$ are the same or different and are each a protective group for the saccharide hydroxyl group; E is methylene or a carbonyl; and A is (A)

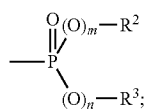

wherein R$^2$ and R$^3$ are the same or different and are each alkyl comprising 1 to 4 carbon atoms or aryl optionally substituted, or R$^2$ and R$^3$ are combined with each other to form an alkylene having 2 or 4 carbon atoms, further wherein the alkylene is optionally substituted with alkyl having 1 to 4 carbon atoms or optionally comprises an intervening phenylene; and m' and n' are each an integer of 0 or 1;

and Q$^{2a}$ is one of the groups given below, (Q$^{2a}$-1)

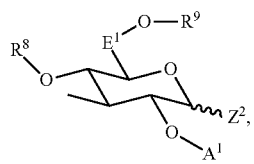

(Q$^{2a}$-2)

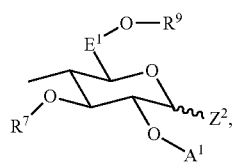

(Q$^{2a}$-3)

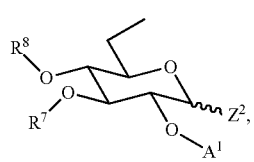

(Q$^{2a}$-4)

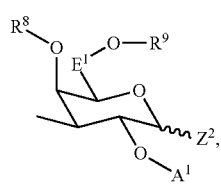

(Q$^{2a}$-5)

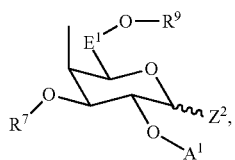

(Q$^{2a}$-6)

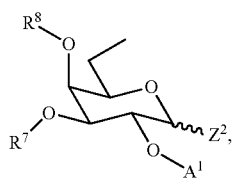

(Q$^{2a}$-7)

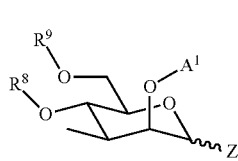

(Q$^{2a}$-8)

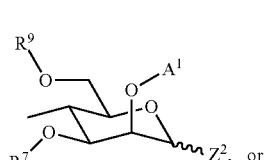, or (Q$^{2a}$-9)

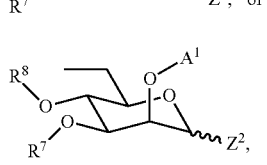

A$^1$ is (A$^1$)

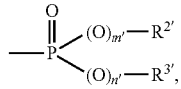

R$^{2'}$ and R$^{3'}$ are the same or different and are each alkyl comprising 1 to 4 carbon atoms or aryl optionally substituted, or R$^{2'}$ and R$^{3'}$ are combined with each other to form an alkylene having 2 or 4 carbon atoms, further wherein the alkylene is optionally substituted with alkyl having 1 to 4 carbon atoms or optionally comprises an intervening phenylene; m' and n' are each an integer of 0 or 1;

R$^7$, R$^8$, R$^9$ are the same or different and are each a protective group for the saccharide hydroxyl group;

E$^1$ is methylene or carbonyl;

Z$^2$ is a group —S—R$^{1'}$, a group —SO—R$^{1'}$, a group —Se—R$^{1'}$, a group —O—C(=NH)CX'$_3$, a halogen atom, an alkoxyl, an alkenyloxy, a group —P(OR$^{1'}$)$_3$ or a group —PO(OR$^{1'}$)$_3$; R$^{1'}$ is an alkyl comprising 1 to 20 carbon atoms, an aryl optionally substituted, or a heteroaromatic group; and X' is a halogen atom.

* * * * *

UNITED STATES PATENT AND TRADEMARK OFFICE
CERTIFICATE OF CORRECTION

| | | |
|---|---|---|
| PATENT NO. | : 8,664,372 B2 | Page 1 of 1 |
| APPLICATION NO. | : 13/477950 | |
| DATED | : March 4, 2014 | |
| INVENTOR(S) | : Yamago | |

It is certified that error appears in the above-identified patent and that said Letters Patent is hereby corrected as shown below:

In the Specification:

Column 24, Line 35: delete "Yield 840" and insert -- Yield 84% --

Signed and Sealed this
Fourteenth Day of October, 2014

Michelle K. Lee
*Deputy Director of the United States Patent and Trademark Office*